(12) United States Patent
Scott et al.

(10) Patent No.: US 6,630,323 B1
(45) Date of Patent: Oct. 7, 2003

(54) NAKED CUTICLE GENES AND THEIR USES

(75) Inventors: Matthew Scott, Stanford, CA (US); Wenlin Zeng, Union City, CA (US); Keith Wharton, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/506,066

(22) Filed: Feb. 17, 2000

Related U.S. Application Data
(60) Provisional application No. 60/120,646, filed on Feb. 17, 1999.

(51) Int. Cl.[7] .......................... C12P 21/06; C12N 15/00; C07H 21/02; C07H 21/04; C07K 1/00
(52) U.S. Cl. .................. 435/69.1; 435/320.1; 435/325; 435/348; 435/455; 536/23.1; 536/23.2; 536/23.5; 536/24.3; 536/24.31; 530/350
(58) Field of Search ............................. 435/320.1, 325, 435/348, 455, 69.1; 536/23.1, 23.5, 24.3, 24.31, 23.2; 530/350

(56) References Cited

U.S. PATENT DOCUMENTS
5,695,933 A * 12/1997 Schalling et al. ............. 435/6

FOREIGN PATENT DOCUMENTS
WO          WO97/17445 A1 *  5/1997          ........... C12N/15/13

OTHER PUBLICATIONS

Bejsovec, A. and Wieschaus, E. Segment Polarity Gene Interactions Modulate Epidermal Patterning in Drosophila Embryos. (1993) Development vol. 119, pp 501–517.*

Gieseler et al. (1995), "Wingless and DWnt4, 2 Drosophila Wnt Genes Have Related Expression, Regulation and Function During the Embryonic Development," *Comptes Rendus de l'Academie des Sciences Serie III Sciences de la Vie,* vol. 318(11):1101–1110.

Limbourg–Bouchon, B. et al. (Jun. 1991), "Interactions Between Fused, a Segment–Polarity Gene in Drosophila, and Other Segmentation Genes," *Development,* vol. 112(2):417–429.

Mack et al. (Jun. 1, 1998), "The Drosophila Naked Gene (nkd) Encodes a Novel Wg–Induced EF–hand Protein which Acts in the Wg Receiving Cells to Inhibit Wg Signaling," *Developmental Biology—SDB Meeting Abstracts,* No. 368, vol. 198(1):221.

Mullen et al. (May 1995), "Establishing Parasegments in Drosophila Embyros: Roles of the Odd–Skipped and naked Genes," *Developmental Biology,* vol. 169(1):295–308.

Wang et al. (1997), "A Genetic and Immunochemical Analysis of the Segment Polarity Gene Naked nkd," *FASEB Journal,* vol. 11(9):A1114, Abstract No. 1505.

Bejsovec et al. (1991), "Roles of *Wingless* in Patterning the Larval Epidermis of *Drosophila*", *Development,* vol. 113:471–485.

Cadigan et al. (1997), "Wnt Signaling: A Common Theme in Animal Development", *Genes & Development,* vol. 11:3286–3305.

DiNardo et al. (1994), "The Making of a Maggot: Patterning the Drosophila Embryonic Epidermis", *Current Opinion in Genetics and Development,* vol. 4:529–534.

Moline et al. (1999), "Directionality of Wingless Protein Transport Influences Epidermal Patterning in the Drosophila Embryo," *Development,* vol. 126:4375–4384.

Pazdera et al. (1998), "Patterned Epidermal Cell Death in Wild–Type and Segment Polarity Mutant Drosophila Embryos", *Development,* vol. 125:3427–3436.

Perrimon et al. (Apr. 1999), "Negative Feedback Mechanisms and Their Roles During Pattern Formation", *Cell,* vol. 97:13–16.

Sanson et al. (Jul. 1999), "Engrailed and Hedgehog Make the Range of Wingless Asymmetric Drosophila Embryos", *Cell,* vol. 98:207–216.

* cited by examiner

*Primary Examiner*—James Ketter
*Assistant Examiner*—M Marvich
(74) *Attorney, Agent, or Firm*—Pamela J. Sherwood; Bozicevic, Field & Francis LLP

(57) ABSTRACT

Methods for isolating naked cuticle genes are provided. The naked cuticle nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as identification of cell type based on expression, and the like.

8 Claims, 5 Drawing Sheets

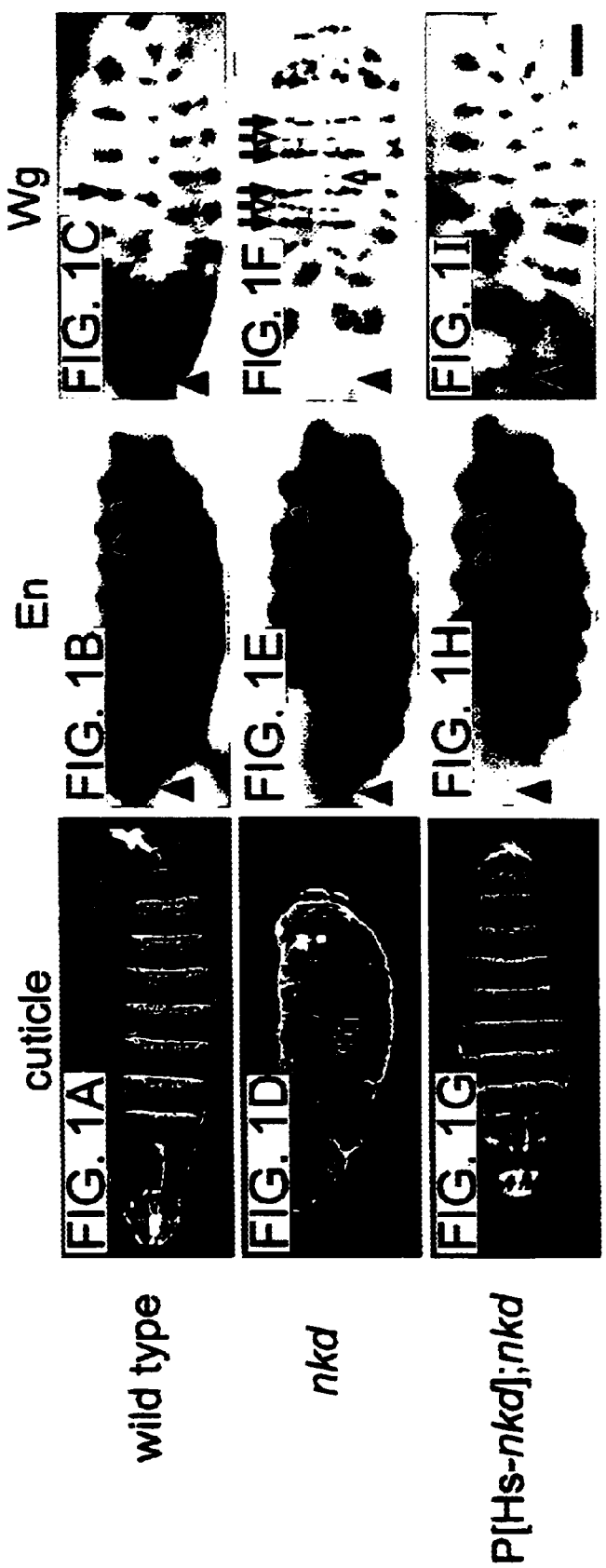

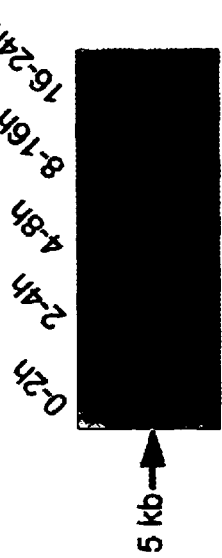
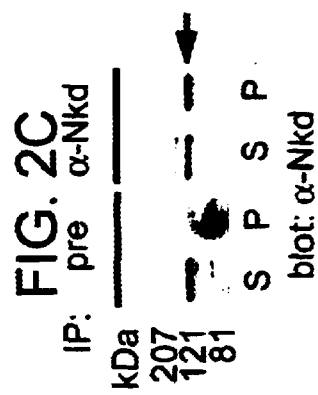
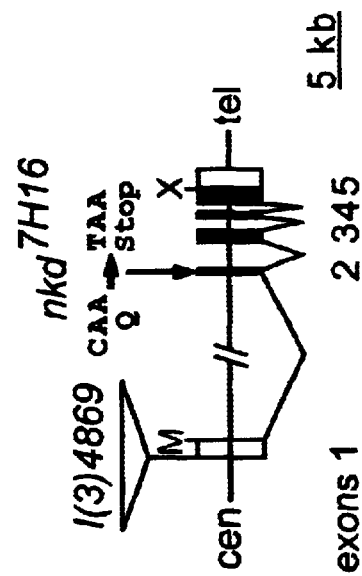
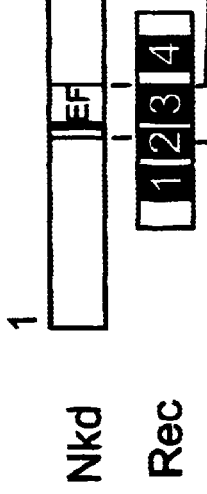

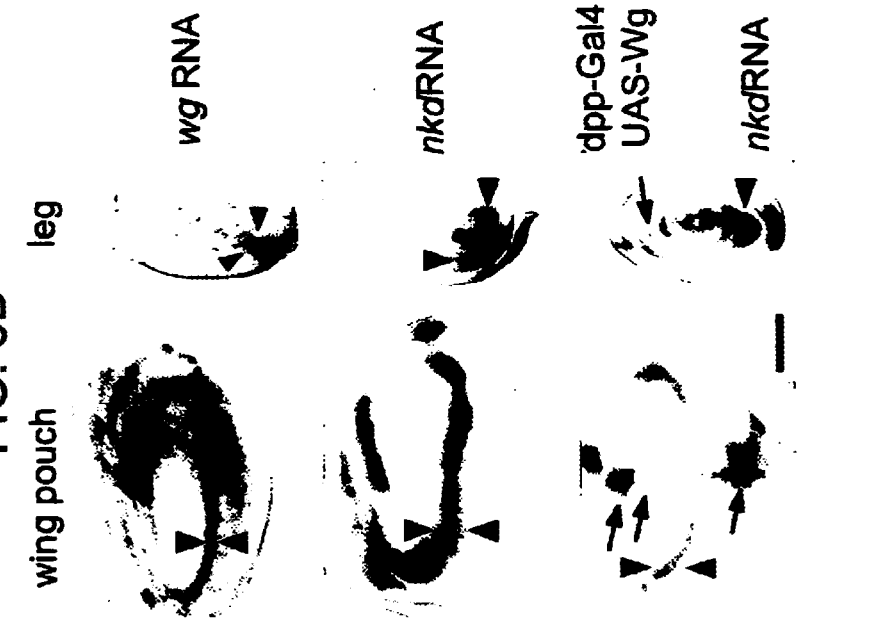
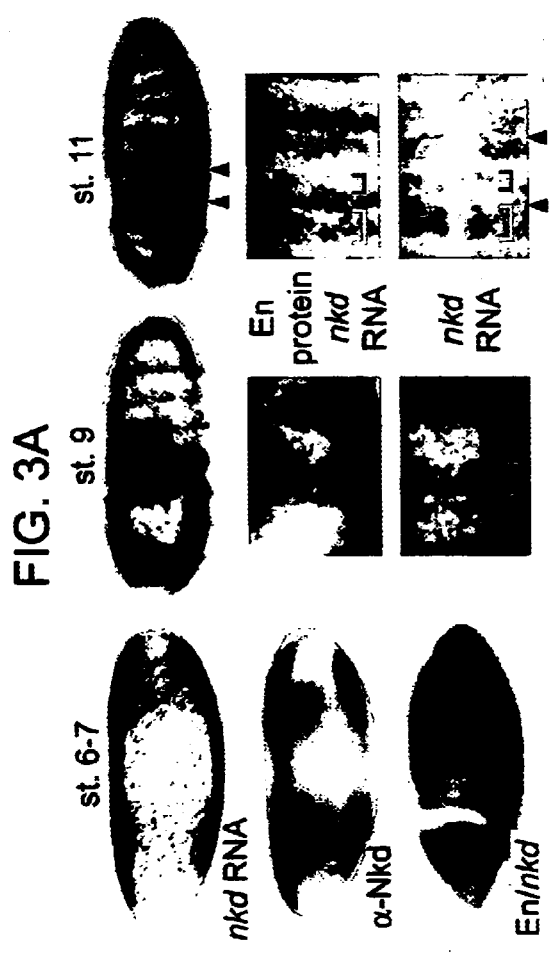

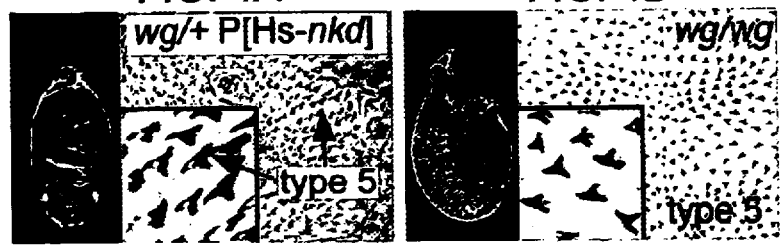
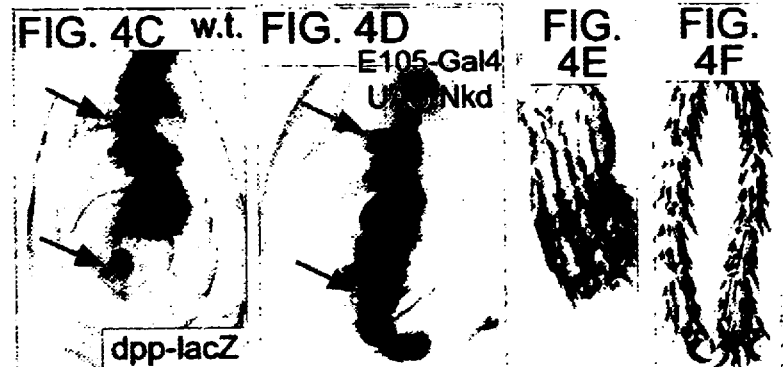
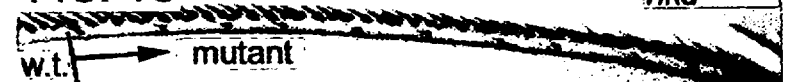
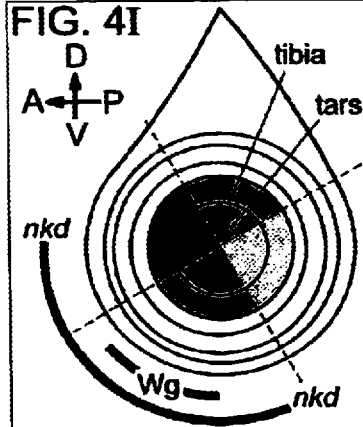
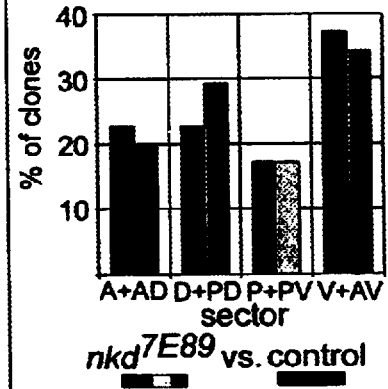
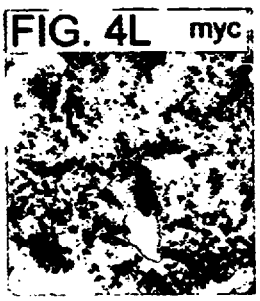
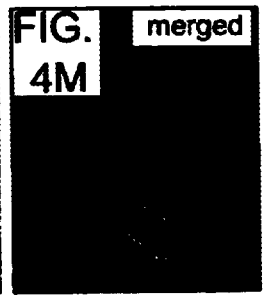

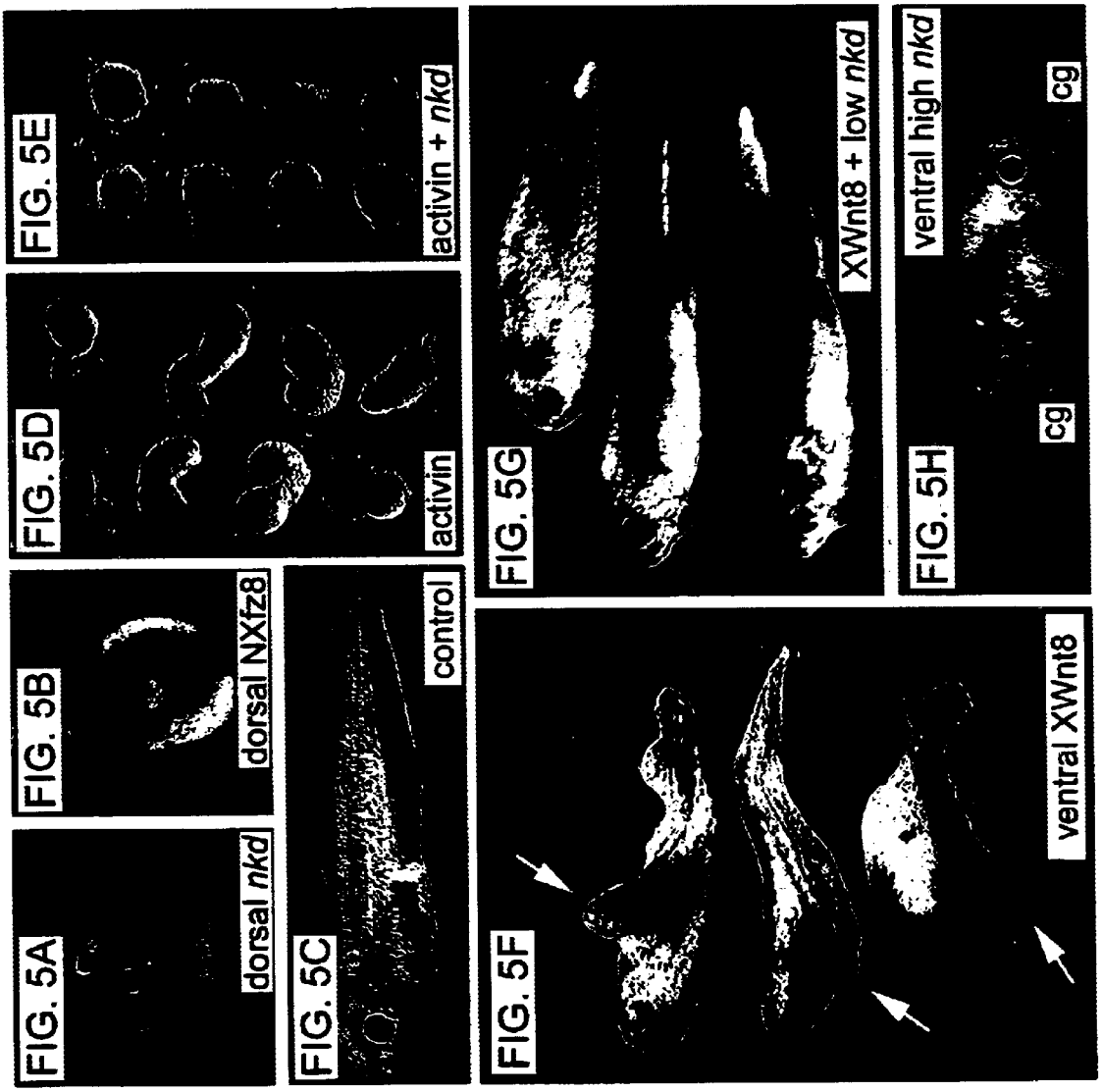

SEQUENCE LISTING

```
<160> NUMBER OF SEQ ID NOS: 15

<210> SEQ ID NO 1
<211> LENGTH: 4954
<212> TYPE: DNA
<213> ORGANISM: Drosophila Melanogaster
<220> FEATURE:
<221> NAME/KEY: CDS
<222> LOCATION: (966)...(3752)

<400> SEQUENCE: 1
ggattgttgt ggcccagtga agttatcgtt gaaattggaa attgatcaaa tgaataaatg      60
tatccgcgag atacgcccag tgaagtttta attttctagc cggagagaaa aatcaagtgt     120 gaaagcaaa aaggaaaaaa cgaaaaacga aaaccgccc ccacaacaat aacaaaaaca       180
accggtacgc cacccccga aaaattgacg tcgccgtcgc cctcgtcgca atcgtttgga      240
aataaatcgt gtttttgcat ttgttgtttt ttgttgttta tacgccaagt tatttacgtc     300
gtcgcaaagc aaaagaaaa aattgaataa ataacaacaa aacggctggc gaaaaacaaa     360
```

-continued

```
tcgagtcggc gaaaatgttt tacaattaaa attacgcgcg cagcgggcac aaaggtacca    420
atatacacga gtgcgagcgc gagtacgagt atctgcaaga tacacacacg tagatcaaat    480
aaagcagcgc aatatgcgca aattaaacta aaatgcagca catcagagct gtaaaaactt    540
ttacgacagc gactacgact ggtaacttgc cacccgcaca gtcgaaaata ataccagata    600
caaattaagg tcgcccagcg gcagcgcata aacacggtgg aacgggaagt ggctgtggaa    660
gtggaagcgg aggattctct cgcctcctac ctggagtata ttagtctcag tccttagatc    720
cttacacaaa aggatagcca gccagggagc gcagaacgca cacacaaggg ccgtaaaaca    780
ttttgggctg ctgctatact gcaggtctcc tcctctcagg actcgtaaat ttccagccca    840
accaccacca ccgccgcccg aaaaacggaa aatagaaaca ccgaaaaatc caagacaccg    900
ccaagtaact gcatcctcaa cccgcttata tatagaacta tataggtaca tatatccggg    960
```

```
cagcg atg gcg ggt aac att gtc aaa tgg tgg aag cat aaa att ctc ggc   1010
      Met Ala Gly Asn Ile Val Lys Trp Trp Lys His Lys Ile Leu Gly
        1               5                  10                  15 ggc tac aaa caa ttc tca gtc cag gaa tgc acc aca gac tcc gag gag    1058
Gly Tyr Lys Gln Phe Ser Val Gln Glu Cys Thr Thr Asp Ser Glu Glu
                20                  25                  30 ctg atg tac cac cag gtg cgg gcc tcc tcc tcc tgc agc gcc ccg ccc    1106
Leu Met Tyr His Gln Val Arg Ala Ser Ser Ser Cys Ser Ala Pro Pro
            35                  40                  45 gat ttg ctg ctg gtc agc gaa cgt gac aat aat atc caa ctg cga tcg    1154
Asp Leu Leu Leu Val Ser Glu Arg Asp Asn Asn Ile Gln Leu Arg Ser
        50                  55                  60 ccg gtg gtg aac ata atc acc acg ccg ccg ggc aat gcg tct ggt gcg    1202
Pro Val Val Asn Ile Ile Thr Thr Pro Pro Gly Asn Ala Ser Gly Ala
    65                  70                  75 gga agt aag cag cag tct cat cac cag acg aac cac cac tcc tcg ggc    1250
Gly Ser Lys Gln Gln Ser His His Gln Thr Asn His His Ser Ser Gly
80                  85                  90                  95 agg agt cat ccc ggg cac acg gca cat ccg cag gat gtg agc agc ggc    1298
Arg Ser His Pro Gly His Thr Ala His Pro Gln Asp Val Ser Ser Gly
                100                 105                 110 ggc agc cat agc aag cat ctg cgc atc agc agc act tcc aat ggc aag    1346
Gly Ser His Ser Lys His Leu Arg Ile Ser Ser Thr Ser Asn Gly Lys
            115                 120                 125 cac ggc aaa tac tca aat atg cag cag caa ctg ccg cag gat gag gat    1394
His Gly Lys Tyr Ser Asn Met Gln Gln Gln Leu Pro Gln Asp Glu Asp
        130                 135                 140 gtg gtg gat gcg gct gcc acg atg cag cag cag cag cac act ggc cac    1442
Val Val Asp Ala Ala Ala Thr Met Gln Gln Gln Gln His Thr Gly His
    145                 150                 155 gcc cac tcg cgc cac ctg cac cac cac aag gag gag cgc atc cga ctg    1490
Ala His Ser Arg His Leu His His His Lys Glu Glu Arg Ile Arg Leu
160                 165                 170                 175 gag gaa ttc acc tgc gac gtg tcc gtg gag ggc ggc aag tca tcg cag    1538
Glu Glu Phe Thr Cys Asp Val Ser Val Glu Gly Gly Lys Ser Ser Gln
                180                 185                 190 ccg ctg cag ttc tcg ttc acg ttc tac gac ctg gac ggg cat cac ggc    1586
Pro Leu Gln Phe Ser Phe Thr Phe Tyr Asp Leu Asp Gly His His Gly
            195                 200                 205 aag ata aca aag gac gac atc gtg ggc att gtg tac acc ata tac gag    1634
Lys Ile Thr Lys Asp Asp Ile Val Gly Ile Val Tyr Thr Ile Tyr Glu
        210                 215                 220 tcc att ggc aag tcg gtg gtg gtg ccc cac tgc ggc agc aag aca atc    1682
Ser Ile Gly Lys Ser Val Val Val Pro His Cys Gly Ser Lys Thr Ile
    225                 230                 235
```

```
aac gtg cgc ctc acc gtc agt ccc gag ggc aaa tcg aaa tcg cag ccg    1730
Asn Val Arg Leu Thr Val Ser Pro Glu Gly Lys Ser Lys Ser Gln Pro
240             245                 250                 255 gtg gtg ccc gtt ccg gtg gca gcc gga ttc agc agc agc cac gcc agc    1778
Val Val Pro Val Pro Val Ala Ala Gly Phe Ser Ser Ser His Ala Ser
            260                 265                 270 aaa ctg aag aag ttg ccc acg ggt ctg gcg gcc atg tcg aaa ccc ctg    1826
Lys Leu Lys Lys Leu Pro Thr Gly Leu Ala Ala Met Ser Lys Pro Leu
        275                 280                 285 gcc ggc gga gga gtg gga tcc ggc gga gcg tcg gcg cta acg aca tcc    1874
Ala Gly Gly Gly Val Gly Ser Gly Gly Ala Ser Ala Leu Thr Thr Ser
                290                 295                 300 gcc ggc aac cgc cgc cag cat cgc tat cga cca cgc aaa ctg att aag    1922
Ala Gly Asn Arg Arg Gln His Arg Tyr Arg Pro Arg Lys Leu Ile Lys
            305                 310                 315 tcc gat gac gag gac gat gac agc aac agc gaa aag gag aag gac gcc    1970
Ser Asp Asp Glu Asp Asp Asp Ser Asn Ser Glu Lys Glu Lys Asp Ala
320                 325                 330                 335 gcc cac gcc cct gcc gcc gac cag ccc agc gga agt gga aca aag gcg    2018
Ala His Ala Pro Ala Ala Asp Gln Pro Ser Gly Ser Gly Thr Lys Ala
                340                 345                 350 act ggg aag agc cat cac cac cag tcg cag tcc gcc agg tat cac cag    2066
Thr Gly Lys Ser His His His Gln Ser Gln Ser Ala Arg Tyr His Gln
            355                 360                 365 aag aac aat tcc cgg gcg gag cag tgc tgc acg gaa cag aat acg ccc    2114
Lys Asn Asn Ser Arg Ala Glu Gln Cys Cys Thr Glu Gln Asn Thr Pro
        370                 375                 380 gac aat ggc cac aat acc tac gag aat atg ctg aat ctc aag tgc tgc    2162
Asp Asn Gly His Asn Thr Tyr Glu Asn Met Leu Asn Leu Lys Cys Cys
385                 390                 395 aag ccg gag gtg gac cag gtg gac tgt ccc tcg cac cga cag cac cac    2210
Lys Pro Glu Val Asp Gln Val Asp Cys Pro Ser His Arg Gln His His
400                 405                 410                 415 cag agc cac ccg aac cat caa atg cgc cag cag gac atc tac atg aaa    2258
Gln Ser His Pro Asn His Gln Met Arg Gln Gln Asp Ile Tyr Met Lys
                420                 425                 430 cag gcc acc cag cgg gtc aag atg ttg cga agg gcg cgc aaa caa aag    2306
Gln Ala Thr Gln Arg Val Lys Met Leu Arg Arg Ala Arg Lys Gln Lys
            435                 440                 445 tac cag gac cac tgc ctc gaa acg cga cag cgc agc ctg tca gtg ggc    2354
Tyr Gln Asp His Cys Leu Glu Thr Arg Gln Arg Ser Leu Ser Val Gly
        450                 455                 460 aac gat tcc gcc tgc ccg aat cgc cat ctg cag ctg cag cag ccg ccg    2402
Asn Asp Ser Ala Cys Pro Asn Arg His Leu Gln Leu Gln Gln Pro Pro
465                 470                 475 gtg ggt cac ccc cag ccc cag tcg ctg aac cac aag agc gcg tcg ggg    2450
Val Gly His Pro Gln Pro Gln Ser Leu Asn His Lys Ser Ala Ser Gly
480                 485                 490                 495 tca cca ccg ctg ggc gtg ggg ggt ggt ggc gac atg atg ctc gat ggg    2498
Ser Pro Pro Leu Gly Val Gly Gly Gly Gly Asp Met Met Leu Asp Gly
                500                 505                 510 gtg cag ctg cgt cag ccg cga ccc cat tcc ctc acc ccg cag cag cat    2546
Val Gln Leu Arg Gln Pro Arg Pro His Ser Leu Thr Pro Gln Gln His
            515                 520                 525 caa cag caa aat cag cag cag cag cag cag cga aaa tcg gcc gag    2594
Gln Gln Gln Asn Gln Gln Gln Gln Gln Gln Arg Lys Ser Ala Glu
        530                 535                 540 tgc tgg aaa tcg gcg ctg aat cgc aac gat tta att agc atc atc agg    2642
Cys Trp Lys Ser Ala Leu Asn Arg Asn Asp Leu Ile Ser Ile Ile Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 545 |     |     |     | 550 |     |     |     | 555 |     |     |     |     |     |     |      |
| gag | agc | atg | gag | aag | aac | cgc | ctg | tgt | ttt | cag | ctg | aat | gga | aaa | ccc | 2690 |
| Glu | Ser | Met | Glu | Lys | Asn | Arg | Leu | Cys | Phe | Gln | Leu | Asn | Gly | Lys | Pro |      |
| 560 |     |     |     |     | 565 |     |     |     | 570 |     |     |     |     | 575 |     |      |
| caa | gcc | aat | gtg | agt | ccc | ata | cgg | caa | ccg | gca | gca | caa | caa | caa | cca | 2738 |
| Gln | Ala | Asn | Val | Ser | Pro | Ile | Arg | Gln | Pro | Ala | Ala | Gln | Gln | Gln | Pro |      |
|     |     |     |     | 580 |     |     |     |     | 585 |     |     |     |     | 590 |     |      |
| caa | caa | cag | caa | cgc | caa | cgc | tgc | aat | acg | ggc | tcg | aaa | ata | ccc | acg | 2786 |
| Gln | Gln | Gln | Gln | Arg | Gln | Arg | Cys | Asn | Thr | Gly | Ser | Lys | Ile | Pro | Thr |      |
|     |     |     | 595 |     |     |     |     | 600 |     |     |     |     | 605 |     |     |      |
| tta | att | acc | aac | cac | agt | ccg | gtc | gcc | cag | cag | tcg | ccg | ctc | agc | tgc | 2834 |
| Leu | Ile | Thr | Asn | His | Ser | Pro | Val | Ala | Gln | Gln | Ser | Pro | Leu | Ser | Cys |      |
|     |     | 610 |     |     |     |     | 615 |     |     |     |     | 620 |     |     |     |      |
| agt | cca | ccc | acg | gcg | gag | ccc | acc | acc | ccc | agc | att | cca | gca | gct | ccg | 2882 |
| Ser | Pro | Pro | Thr | Ala | Glu | Pro | Thr | Thr | Pro | Ser | Ile | Pro | Ala | Ala | Pro |      |
| 625 |     |     |     |     | 630 |     |     |     | 635 |     |     |     |     |     |     |      |
| ccg | gcc | atc | gag | gtc | aac | ggt | cag | cag | cac | cac | ccc | act | cat | ccc | act | 2930 |
| Pro | Ala | Ile | Glu | Val | Asn | Gly | Gln | Gln | His | His | Pro | Thr | His | Pro | Thr |      |
| 640 |     |     |     |     | 645 |     |     |     | 650 |     |     |     |     | 655 |     |      |
| cat | ccc | agc | cac | cac | aac | cac | cac | gag | cat | ccc | caa | ccg | cac | ata | cct | 2978 |
| His | Pro | Ser | His | His | Asn | His | His | Glu | His | Pro | Gln | Pro | His | Ile | Pro |      |
|     |     |     | 660 |     |     |     |     | 665 |     |     |     |     | 670 |     |     |      |
| atc | tac | cat | cag | cag | ttg | gcc | att | aat | ccg | gcc | gtc | ctg | gcc | gcc | cag | 3026 |
| Ile | Tyr | His | Gln | Gln | Leu | Ala | Ile | Asn | Pro | Ala | Val | Leu | Ala | Ala | Gln |      |
|     |     |     | 675 |     |     |     |     | 680 |     |     |     |     | 685 |     |     |      |
| cag | acg | cac | aac | acg | gcc | cac | aac | aag | ctg | aat | ctg | tgt | ggc | tac | gac | 3074 |
| Gln | Thr | His | Asn | Thr | Ala | His | Asn | Lys | Leu | Asn | Leu | Cys | Gly | Tyr | Asp |      |
|     |     |     | 690 |     |     |     |     | 695 |     |     |     |     | 700 |     |     |      |
| tcc | ttt | ctg | cac | gcc | act | atc | tgt | ggg | ggc | ggt | gca | gcc | gcc | cac | tcg | 3122 |
| Ser | Phe | Leu | His | Ala | Thr | Ile | Cys | Gly | Gly | Gly | Ala | Ala | Ala | His | Ser |      |
|     | 705 |     |     |     |     | 710 |     |     |     |     | 715 |     |     |     |     |      |
| ccc | ccg | gcc | acg | ccc | agt | aat | gtg | gcg | acc | gtt | cag | ccg | ata | ccc | aag | 3170 |
| Pro | Pro | Ala | Thr | Pro | Ser | Asn | Val | Ala | Thr | Val | Gln | Pro | Ile | Pro | Lys |      |
| 720 |     |     |     |     | 725 |     |     |     | 730 |     |     |     |     | 735 |     |      |
| aag | agc | cag | aag | aac | ctg | ctg | caa | gga | tac | cag | cgt | ttg | gag | cag | tcg | 3218 |
| Lys | Ser | Gln | Lys | Asn | Leu | Leu | Gln | Gly | Tyr | Gln | Arg | Leu | Glu | Gln | Ser |      |
|     |     |     |     | 740 |     |     |     |     | 745 |     |     |     |     | 750 |     |      |
| cag | cag | cag | cag | caa | cag | cag | cgg | agc | agc | aag | gac | tac | aag | aac | tat | 3266 |
| Gln | Gln | Gln | Gln | Gln | Gln | Gln | Arg | Ser | Ser | Lys | Asp | Tyr | Lys | Asn | Tyr |      |
|     |     | 755 |     |     |     |     | 760 |     |     |     |     | 765 |     |     |     |      |
| ggc | aac | ctc | atc | tat | gcc | aag | ctg | agt | gag | cag | ctg | cag | cag | aag | gat | 3314 |
| Gly | Asn | Leu | Ile | Tyr | Ala | Lys | Leu | Ser | Glu | Gln | Leu | Gln | Gln | Lys | Asp |      |
|     |     | 770 |     |     |     |     | 775 |     |     |     |     | 780 |     |     |     |      |
| cgg | gag | cag | agg | cga | cag | cgg | cac | aag | cag | cag | caa | cac | cag | atg | ctg | 3362 |
| Arg | Glu | Gln | Arg | Arg | Gln | Arg | His | Lys | Gln | Gln | Gln | His | Gln | Met | Leu |      |
|     | 785 |     |     |     |     | 790 |     |     |     |     | 795 |     |     |     |     |      |
| cag | gat | cag | ccc | aag | gat | gcg | agt | cgg | tcg | gag | cag | cga | cca | ccg | aca | 3410 |
| Gln | Asp | Gln | Pro | Lys | Asp | Ala | Ser | Arg | Ser | Glu | Gln | Arg | Pro | Pro | Thr |      |
| 800 |     |     |     |     | 805 |     |     |     | 810 |     |     |     |     | 815 |     |      |
| tca | aac | tcc | agt | tcg | gct | ggc | tcc | aag | atc | tac | ggc | gat | gcc | gtc | gag | 3458 |
| Ser | Asn | Ser | Ser | Ser | Ala | Gly | Ser | Lys | Ile | Tyr | Gly | Asp | Ala | Val | Glu |      |
|     |     |     |     | 820 |     |     |     |     | 825 |     |     |     |     | 830 |     |      |
| tgc | gcc | cat | cta | ctg | gcc | agc | gag | gag | gag | gac | cta | ccc | ccc | agt | ccg | 3506 |
| Cys | Ala | His | Leu | Leu | Ala | Ser | Glu | Glu | Glu | Asp | Leu | Pro | Pro | Ser | Pro |      |
|     |     |     | 835 |     |     |     |     | 840 |     |     |     |     | 845 |     |     |      |
| cag | ctg | acc | agt | acg | ccc | agc | aaa | gtg | gtc | agc | acg | gac | acc | ctc | atc | 3554 |
| Gln | Leu | Thr | Ser | Thr | Pro | Ser | Lys | Val | Val | Ser | Thr | Asp | Thr | Leu | Ile |      |
|     |     | 850 |     |     |     |     | 855 |     |     |     |     | 860 |     |     |     |      |
| aat | ctc | aac | gac | gat | gtg | ggc | gag | gct | gtg | gcc | gag | gca | gtt | aca | gaa | 3602 |

| | | | | | | | | | | | | |
|---|---|---|---|---|---|---|---|---|---|---|---|---|
| Asn | Leu | Asn | Asp | Asp | Val | Gly | Glu | Ala | Val | Ala | Glu | Ala | Val | Thr | Glu |
| | 865 | | | | 870 | | | | 875 | | | | | | |

```
gga ggc aag cag tcg ttg gag gct gag gaa tct ggc cag cag gtg gag       3650
Gly Gly Lys Gln Ser Leu Glu Ala Glu Glu Ser Gly Gln Gln Val Glu
880             885             890             895 gtg gaa ctg gac acc agc gcc tcc agc tcc atg ata cac cgc tat gtg       3698
Val Glu Leu Asp Thr Ser Ala Ser Ser Ser Met Ile His Arg Tyr Val
        900             905             910 cac gag cac atc cac cac cac tat cac cac ttc aag gag cag cag gat       3746
His Glu His Ile His His His Tyr His His Phe Lys Glu Gln Gln Asp
            915             920             925 gtc tag gctaatcggg gaatcacact ataaactatt tgaatgttgc ttatgtttca        3802
Val * gtctattgat taatgtagcg cgaattgtaa tttaaagtaa gccttcatca actaaaacga     3862
gaaaatattc gaaaaacgat attagggcca gaaacagtgg ggttggttaa gtgagtttgg    3922
agtttggtta accaaagaca aattgagaac gattgctgac aaaaatcaat tgatagaaat    3982
gctagatact aaataaaata actgattatt attctttgat tttgtaaaac caatatgtaa    4042
attaggataa atattaaacc taacacagtg aagttaagct aggttcctga ataggtaaag    4102
aggttaacca atttcaaact cgcatctcca atttctctca aggaaaatct ttagaaccaa    4162
attctaactc aatgaagatt tagcccactg tgagatccac tgatcccagc atatacatac    4222
atacatacat acacatagcc tctatagctt acgcagaatt cgaaagaaaa caaaaatcat    4282
gcgccttttg ccttagcaac aatcgaatcg ccgcttcgct atgctacatg ttgcagaaac    4342
acatatcact atcagaaaca acatgttgcc aagagcattt tgtgttgctg agcgtgtacg    4402
tgtaaactaa tgggagaaaa actattgttt agtgcaaatt attaaacaa attgttgtct     4462 atgatataaa gttttatgcg ccgctttta cgtgtttaga cagagagcaa cagatgattg     4522
tagtggaact atggccgcca gtttaagtta actaccgata tggatcatgt atatttatgt   4582
tatctaagcc aattaattta aatactattc ttagtttcta acactaaccc caaacaagac    4642
aagaaacaat gcaactaagt actaaaccac aacgaccacc aacacaaatc gtagttcaat    4702
tattatttta aaacttgttt ttaattacat catctgtcaa acaatcgagt taccaatcca   4762
atcaatcaaa caaacaaaag aagcacaaaa acaaaatgca tttaactctt atttacataa    4822
aaaagactga tttccaatta aacaatatat taattaattg catatgaata aaggtatata    4882
taaatatata tagacaattt atgagaaata ctaaataaat tattgaattg ctaaaaagaa    4942
aaaaaaaaaa aa                                                         4954

<210> SEQ ID NO 2
<211> LENGTH: 928
<212> TYPE: PRT
<213> ORGANISM: Drosophila Melanogaster

<400> SEQUENCE: 2

Met Ala Gly Asn Ile Val Lys Trp Trp Lys His Lys Ile Leu Gly Gly
 1               5                  10                  15

Tyr Lys Gln Phe Ser Val Gln Glu Cys Thr Thr Asp Ser Glu Glu Leu
                20                  25                  30

Met Tyr His Gln Val Arg Ala Ser Ser Cys Ser Ala Pro Pro Asp
            35                  40                  45

Leu Leu Leu Val Ser Glu Arg Asp Asn Asn Ile Gln Leu Arg Ser Pro
        50                  55                  60

Val Val Asn Ile Ile Thr Thr Pro Pro Gly Asn Ala Ser Gly Ala Gly
```

```
              65                  70                  75                  80
Ser Lys Gln Gln Ser His His Gln Thr Asn His His Ser Ser Gly Arg
                85                  90                  95

Ser His Pro Gly His Thr Ala His Pro Gln Asp Val Ser Ser Gly Gly
            100                 105                 110

Ser His Ser Lys His Leu Arg Ile Ser Ser Thr Ser Asn Gly Lys His
            115                 120                 125

Gly Lys Tyr Ser Asn Met Gln Gln Leu Pro Gln Asp Glu Asp Val
        130                 135                 140

Val Asp Ala Ala Ala Thr Met Gln Gln Gln His Thr Gly His Ala
145                 150                 155                 160

His Ser Arg His Leu His His His Lys Glu Glu Arg Ile Arg Leu Glu
                165                 170                 175

Glu Phe Thr Cys Asp Val Ser Val Glu Gly Lys Ser Ser Gln Pro
            180                 185                 190

Leu Gln Phe Ser Phe Thr Phe Tyr Asp Leu Asp Gly His His Gly Lys
            195                 200                 205

Ile Thr Lys Asp Asp Ile Val Gly Ile Val Tyr Thr Ile Tyr Glu Ser
        210                 215                 220

Ile Gly Lys Ser Val Val Pro His Cys Gly Ser Lys Thr Ile Asn
225                 230                 235                 240

Val Arg Leu Thr Val Ser Pro Glu Gly Lys Ser Lys Ser Gln Pro Val
                245                 250                 255

Val Pro Val Pro Val Ala Ala Gly Phe Ser Ser Ser His Ala Ser Lys
            260                 265                 270

Leu Lys Lys Leu Pro Thr Gly Leu Ala Ala Met Ser Lys Pro Leu Ala
        275                 280                 285

Gly Gly Gly Val Gly Ser Gly Gly Ala Ser Ala Leu Thr Thr Ser Ala
        290                 295                 300

Gly Asn Arg Arg Gln His Arg Tyr Arg Pro Arg Lys Leu Ile Lys Ser
305                 310                 315                 320

Asp Asp Glu Asp Asp Ser Asn Ser Glu Lys Glu Lys Asp Ala Ala
            325                 330                 335

His Ala Pro Ala Ala Asp Gln Pro Ser Gly Ser Gly Thr Lys Ala Thr
            340                 345                 350

Gly Lys Ser His His His Gln Ser Gln Ser Ala Arg Tyr His Gln Lys
        355                 360                 365

Asn Asn Ser Arg Ala Glu Gln Cys Cys Thr Glu Gln Asn Thr Pro Asp
        370                 375                 380

Asn Gly His Asn Thr Tyr Glu Asn Met Leu Asn Leu Lys Cys Cys Lys
385                 390                 395                 400

Pro Glu Val Asp Gln Val Asp Cys Pro Ser His Arg Gln His His Gln
            405                 410                 415

Ser His Pro Asn His Gln Met Arg Gln Gln Asp Ile Tyr Met Lys Gln
            420                 425                 430

Ala Thr Gln Arg Val Lys Met Leu Arg Arg Ala Arg Lys Gln Lys Tyr
        435                 440                 445

Gln Asp His Cys Leu Glu Thr Arg Gln Arg Ser Leu Ser Val Gly Asn
        450                 455                 460

Asp Ser Ala Cys Pro Asn Arg His Leu Gln Leu Gln Gln Pro Pro Val
465                 470                 475                 480

Gly His Pro Gln Pro Gln Ser Leu Asn His Lys Ser Ala Ser Gly Ser
            485                 490                 495
```

-continued

```
Pro Pro Leu Gly Val Gly Gly Gly Asp Met Met Leu Asp Gly Val
            500                 505                 510
Gln Leu Arg Gln Pro Arg Pro His Ser Leu Thr Pro Gln Gln His Gln
        515                 520                 525
Gln Gln Asn Gln Gln Gln Gln Gln Gln Arg Lys Ser Ala Glu Cys
    530                 535                 540
Trp Lys Ser Ala Leu Asn Arg Asn Asp Leu Ile Ser Ile Ile Arg Glu
545                 550                 555                 560
Ser Met Glu Lys Asn Arg Leu Cys Phe Gln Leu Asn Gly Lys Pro Gln
                565                 570                 575
Ala Asn Val Ser Pro Ile Arg Gln Pro Ala Ala Gln Gln Gln Pro Gln
            580                 585                 590
Gln Gln Gln Arg Gln Arg Cys Asn Thr Gly Ser Lys Ile Pro Thr Leu
        595                 600                 605
Ile Thr Asn His Ser Pro Val Ala Gln Gln Ser Pro Leu Ser Cys Ser
    610                 615                 620
Pro Pro Thr Ala Glu Pro Thr Thr Pro Ser Ile Pro Ala Ala Pro Pro
625                 630                 635                 640
Ala Ile Glu Val Asn Gly Gln Gln His His Pro Thr His Pro Thr His
                645                 650                 655
Pro Ser His His Asn His His Glu His Pro Gln Pro His Ile Pro Ile
            660                 665                 670
Tyr His Gln Gln Leu Ala Ile Asn Pro Ala Val Leu Ala Ala Gln Gln
        675                 680                 685
Thr His Asn Thr Ala His Asn Lys Leu Asn Leu Cys Gly Tyr Asp Ser
    690                 695                 700
Phe Leu His Ala Thr Ile Cys Gly Gly Gly Ala Ala Ala His Ser Pro
705                 710                 715                 720
Pro Ala Thr Pro Ser Asn Val Ala Thr Val Gln Pro Ile Pro Lys Lys
                725                 730                 735
Ser Gln Lys Asn Leu Leu Gln Gly Tyr Gln Arg Leu Glu Gln Ser Gln
            740                 745                 750
Gln Gln Gln Gln Gln Gln Arg Ser Ser Lys Asp Tyr Lys Asn Tyr Gly
        755                 760                 765
Asn Leu Ile Tyr Ala Lys Leu Ser Glu Gln Leu Gln Gln Lys Asp Arg
    770                 775                 780
Glu Gln Arg Arg Gln Arg His Lys Gln Gln Gln His Gln Met Leu Gln
785                 790                 795                 800
Asp Gln Pro Lys Asp Ala Ser Arg Ser Glu Gln Arg Pro Pro Thr Ser
                805                 810                 815
Asn Ser Ser Ser Ala Gly Ser Lys Ile Tyr Gly Asp Ala Val Glu Cys
            820                 825                 830
Ala His Leu Leu Ala Ser Glu Glu Asp Leu Pro Pro Ser Pro Gln
        835                 840                 845
Leu Thr Ser Thr Pro Ser Lys Val Val Ser Thr Asp Thr Leu Ile Asn
    850                 855                 860
Leu Asn Asp Asp Val Gly Glu Ala Val Ala Glu Ala Val Thr Glu Gly
865                 870                 875                 880
Gly Lys Gln Ser Leu Glu Ala Glu Ser Gly Gln Gln Val Glu Val
                885                 890                 895
Glu Leu Asp Thr Ser Ala Ser Ser Met Ile His Arg Tyr Val His
            900                 905                 910
```

```
                                                                   -continued Glu His Ile His His His Tyr His His Phe Lys Glu Gln Gln Asp Val
        915                 920                 925

<210> SEQ ID NO 3
<211> LENGTH: 1731
<212> TYPE: DNA
<213> ORGANISM: Mus musculus
<220> FEATURE:
<221> NAME/KEY: CDS
<222> LOCATION: (140)...(1553)
<223> OTHER INFORMATION: Nkd1 coding sequence

<400> SEQUENCE: 3
gaattccgcg gccggagcgc gtcccggcgc cgcctaaggc tgcgctcggc gcgcggactg        60
tgaggaggag gcgagcgagg ctggcgcggg gtcggcggcc ggacgcatgg cttaggacgc       120
tccgccgccg cgccccagc atg ggg aaa ctt cac tcg aag ccg gcc gcc gtg       172
                    Met Gly Lys Leu His Ser Lys Pro Ala Ala Val
                      1               5                      10 tgc aag cgc agg gag agc ccg gaa ggt gac agc ttt gct gta agc gct       220
Cys Lys Arg Arg Glu Ser Pro Glu Gly Asp Ser Phe Ala Val Ser Ala
             15                  20                  25 gct tgg gca agg aaa ggc atc gag gag tgg atc ggg agg cag cgc tgt       268
Ala Trp Ala Arg Lys Gly Ile Glu Glu Trp Ile Gly Arg Gln Arg Cys
 30                  35                  40 cca ggc agc gtc tca gga ccc cgt cag ctg aga ttg gca ggc act gtt       316
Pro Gly Ser Val Ser Gly Pro Arg Gln Leu Arg Leu Ala Gly Thr Val
         45                  50                  55 ggt cga ggc act cgg gaa ctc gtg ggt gac act tct aga gag gct ctc       364
Gly Arg Gly Thr Arg Glu Leu Val Gly Asp Thr Ser Arg Glu Ala Leu
 60                  65                  70                  75 ggt gag gag gac gag gac gac ttc ccc cta gaa gtg gcc ctg ccg cct       412
Gly Glu Glu Asp Glu Asp Asp Phe Pro Leu Glu Val Ala Leu Pro Pro
                 80                  85                  90 gag aag atc gac agc cta ggt agt gga gat gag aag aga atg gag aga       460
Glu Lys Ile Asp Ser Leu Gly Ser Gly Asp Glu Lys Arg Met Glu Arg
             95                 100                 105 ctg agc gaa cct ggc cag gcc tcc aag aag cag ctc aag ttt gaa gag       508
Leu Ser Glu Pro Gly Gln Ala Ser Lys Lys Gln Leu Lys Phe Glu Glu
        110                 115                 120 cta cag tgt gat gtc tct gtg gag gag gac agc cgg caa gag tgg act       556
Leu Gln Cys Asp Val Ser Val Glu Glu Asp Ser Arg Gln Glu Trp Thr
125                 130                 135 ttc act cta tat gac ttc cac aac aat ggc aaa gtg acc cgt gag gac       604
Phe Thr Leu Tyr Asp Phe His Asn Asn Gly Lys Val Thr Arg Glu Asp
140                 145                 150                 155 att acc agc ttg ctg cat acc atc tat gaa gtg gtt gac tcc tct gtg       652
Ile Thr Ser Leu Leu His Thr Ile Tyr Glu Val Val Asp Ser Ser Val
                160                 165                 170 aac cat tcc ccc aca tca agc aag aca ctg cgg gtg aag ctc acc gtg       700
Asn His Ser Pro Thr Ser Ser Lys Thr Leu Arg Val Lys Leu Thr Val
            175                 180                 185 gct cct gac ggg agc cag agt aag agg agc gtc ctt ttc aac cat acc       748
Ala Pro Asp Gly Ser Gln Ser Lys Arg Ser Val Leu Phe Asn His Thr
        190                 195                 200 gat ctg cag agc aca agg ccc cga gca gac acc aaa ccc gct gag gag       796
Asp Leu Gln Ser Thr Arg Pro Arg Ala Asp Thr Lys Pro Ala Glu Glu
    205                 210                 215 ctg cgt ggc tgg gag aag aag cag cga gcc cca ctc agg ttc cag ggt       844
Leu Arg Gly Trp Glu Lys Lys Gln Arg Ala Pro Leu Arg Phe Gln Gly
220                 225                 230                 235
```

```
gac agc cac ctg gag cag cca gac tgc tac cac cat tgc gtg gat gag    892
Asp Ser His Leu Glu Gln Pro Asp Cys Tyr His His Cys Val Asp Glu
            240                 245                 250 aac att gag agg aga aac cac tac cta gac ctg gcg ggg ata gag aac    940
Asn Ile Glu Arg Arg Asn His Tyr Leu Asp Leu Ala Gly Ile Glu Asn
        255                 260                 265 tac acg tct cag ttt gga ccg gga tcc cct tcg gtg gcc cag aag tca    988
Tyr Thr Ser Gln Phe Gly Pro Gly Ser Pro Ser Val Ala Gln Lys Ser
    270                 275                 280 gag ctg ccc cct cga atc tcc aac ccc act cgc tct cgc tcc cac gag   1036
Glu Leu Pro Pro Arg Ile Ser Asn Pro Thr Arg Ser Arg Ser His Glu
285                 290                 295 cca gaa gct gcc cac atc cca cac cgg agg ccc caa ggt gtg gac cca   1084
Pro Glu Ala Ala His Ile Pro His Arg Arg Pro Gln Gly Val Asp Pro
300                 305                 310                 315 ggc tcc ttc cac ctc ctt gac acc cca ttt gcc aag gca tca gag ctc   1132
Gly Ser Phe His Leu Leu Asp Thr Pro Phe Ala Lys Ala Ser Glu Leu
            320                 325                 330 cag caa cgg ctc cgg ggc act cag gat ggg agc aag cac ttt gtg agg   1180
Gln Gln Arg Leu Arg Gly Thr Gln Asp Gly Ser Lys His Phe Val Arg
        335                 340                 345 tcc ccc aag gcc cag ggc aag aac atg ggt atg ggc cac ggg gcc aga   1228
Ser Pro Lys Ala Gln Gly Lys Asn Met Gly Met Gly His Gly Ala Arg
    350                 355                 360 ggt gca aga agc aag cct cca ctg gta ccc acc acc cat act gtc tcc   1276
Gly Ala Arg Ser Lys Pro Pro Leu Val Pro Thr Thr His Thr Val Ser
365                 370                 375 ccc tct gcc cat ctg gcc acc agc cca gcc ctt ctc ccc acc ctg gca   1324
Pro Ser Ala His Leu Ala Thr Ser Pro Ala Leu Leu Pro Thr Leu Ala
380                 385                 390                 395 ccc ctg ggg cac aag aaa cac aag cat cga gcc aag gag agc cag gcg   1372
Pro Leu Gly His Lys Lys His Lys His Arg Ala Lys Glu Ser Gln Ala
            400                 405                 410 agc tgc cgg ggc ctg cag ggc ccc ctg gct gca gga ggc tcc acc gtc   1420
Ser Cys Arg Gly Leu Gln Gly Pro Leu Ala Ala Gly Gly Ser Thr Val
        415                 420                 425 atg ggg cgg gag cag gtg agg gag ctg cct gcc gtg atg gtg tac gag   1468
Met Gly Arg Glu Gln Val Arg Glu Leu Pro Ala Val Met Val Tyr Glu
    430                 435                 440 agc cag gct agg cag gcc gtc cag aga cac gaa cac cat cac cac cac   1516
Ser Gln Ala Arg Gln Ala Val Gln Arg His Glu His His His His His
445                 450                 455 gaa cat cac cac cat tat cac cac ttc tat cag ccc t agaccccagc      1563
Glu His His His His Tyr His His Phe Tyr Gln Pro
460                 465                 470 aggctgccac gggaaggacc cagcccacac cctaaggcat tattattcta ttaattattg  1623
ttattatggc aattattgtt attaataatt attgttactc cactaatatt tagccagcct  1683
tcatgtagaa gacacatgga aacacagaag taaactttta tggaattc              1731

<210> SEQ ID NO 4
<211> LENGTH: 471
<212> TYPE: PRT
<213> ORGANISM: Mus musculus

<400> SEQUENCE: 4

Met Gly Lys Leu His Ser Lys Pro Ala Ala Val Cys Lys Arg Arg Glu
1               5                   10                  15

Ser Pro Glu Gly Asp Ser Phe Ala Val Ser Ala Ala Trp Ala Arg Lys
            20                  25                  30
```

-continued

```
Gly Ile Glu Glu Trp Ile Gly Arg Gln Arg Cys Pro Gly Ser Val Ser
        35                  40                  45
Gly Pro Arg Gln Leu Arg Leu Ala Gly Thr Val Gly Arg Gly Thr Arg
 50                  55                  60
Glu Leu Val Gly Asp Thr Ser Arg Glu Ala Leu Gly Glu Glu Asp Glu
65                   70                  75                  80
Asp Asp Phe Pro Leu Glu Val Ala Leu Pro Pro Glu Lys Ile Asp Ser
                 85                  90                  95
Leu Gly Ser Gly Asp Glu Lys Arg Met Glu Arg Leu Ser Glu Pro Gly
            100                 105                 110
Gln Ala Ser Lys Lys Gln Leu Lys Phe Glu Glu Leu Gln Cys Asp Val
        115                 120                 125
Ser Val Glu Glu Asp Ser Arg Gln Glu Trp Thr Phe Thr Leu Tyr Asp
    130                 135                 140
Phe His Asn Asn Gly Lys Val Thr Arg Glu Asp Ile Thr Ser Leu Leu
145                 150                 155                 160
His Thr Ile Tyr Glu Val Val Asp Ser Ser Val Asn His Ser Pro Thr
                165                 170                 175
Ser Ser Lys Thr Leu Arg Val Lys Leu Thr Val Ala Pro Asp Gly Ser
            180                 185                 190
Gln Ser Lys Arg Ser Val Leu Phe Asn His Thr Asp Leu Gln Ser Thr
        195                 200                 205
Arg Pro Arg Ala Asp Thr Lys Pro Ala Glu Leu Arg Gly Trp Glu
    210                 215                 220
Lys Lys Gln Arg Ala Pro Leu Arg Phe Gln Gly Asp Ser His Leu Glu
225                 230                 235                 240
Gln Pro Asp Cys Tyr His His Cys Val Asp Glu Asn Ile Glu Arg Arg
                245                 250                 255
Asn His Tyr Leu Asp Leu Ala Gly Ile Glu Asn Tyr Thr Ser Gln Phe
            260                 265                 270
Gly Pro Gly Ser Pro Ser Val Ala Gln Lys Ser Glu Leu Pro Pro Arg
        275                 280                 285
Ile Ser Asn Pro Thr Arg Ser Arg Ser His Glu Pro Glu Ala Ala His
    290                 295                 300
Ile Pro His Arg Arg Pro Gln Gly Val Asp Pro Gly Ser Phe His Leu
305                 310                 315                 320
Leu Asp Thr Pro Phe Ala Lys Ala Ser Glu Leu Gln Gln Arg Leu Arg
                325                 330                 335
Gly Thr Gln Asp Gly Ser Lys His Phe Val Arg Ser Pro Lys Ala Gln
            340                 345                 350
Gly Lys Asn Met Gly Met Gly His Gly Ala Arg Gly Ala Arg Ser Lys
        355                 360                 365
Pro Pro Leu Val Pro Thr Thr His Thr Val Ser Pro Ser Ala His Leu
    370                 375                 380
Ala Thr Ser Pro Ala Leu Leu Pro Thr Leu Ala Pro Leu Gly His Lys
385                 390                 395                 400
Lys His Lys His Arg Ala Lys Glu Ser Gln Ala Ser Cys Arg Gly Leu
                405                 410                 415
Gln Gly Pro Leu Ala Ala Gly Gly Ser Thr Val Met Gly Arg Glu Gln
            420                 425                 430
Val Arg Glu Leu Pro Ala Val Met Val Tyr Glu Ser Gln Ala Arg Gln
        435                 440                 445
```

```
Ala Val Gln Arg His Glu His His His His Glu His His His
    450                 455                 460
Tyr His His Phe Tyr Gln Pro
465                 470

<210> SEQ ID NO 5
<211> LENGTH: 1438
<212> TYPE: DNA
<213> ORGANISM: Homo sapiens
<220> FEATURE:
<221> NAME/KEY: CDS
<222> LOCATION: (8)...(1418)
<223> OTHER INFORMATION: Nkd1 coding sequence

<400> SEQUENCE: 5 ccccagc atg ggg aaa ctt cac tcc aag ccg gcc gcc gtg tgc aag cgc      49
        Met Gly Lys Leu His Ser Lys Pro Ala Ala Val Cys Lys Arg
        1               5                   10 agg gag agc ccg gaa ggt gac agc ttc gcc gtg agc gct gcc tgg gct      97
Arg Glu Ser Pro Glu Gly Asp Ser Phe Ala Val Ser Ala Ala Trp Ala
15                  20                  25                  30 cgg aag ggc atc gag gag tgg atc ggg aga cag cgc tgc ccg ggc ggt     145
Arg Lys Gly Ile Glu Glu Trp Ile Gly Arg Gln Arg Cys Pro Gly Gly
                35                  40                  45 gtc tcg gga ccc cga cag ctg cgg ttg gcg ggc acc ata ggc cga agc     193
Val Ser Gly Pro Arg Gln Leu Arg Leu Ala Gly Thr Ile Gly Arg Ser
            50                  55                  60 acc cgg gag ctc gtg ggc gac gtg ttg aga gac acg ctc agc gag gaa     241
Thr Arg Glu Leu Val Gly Asp Val Leu Arg Asp Thr Leu Ser Glu Glu
        65                  70                  75 gag gag gac gac ttt cgg ctg gaa gtg gcc ctg cct cct gag aag act     289
Glu Glu Asp Asp Phe Arg Leu Glu Val Ala Leu Pro Pro Glu Lys Thr
    80                  85                  90 gac ggg ctg ggc agc gga gat gag aag aag atg gag aga gtg agc gaa     337
Asp Gly Leu Gly Ser Gly Asp Glu Lys Lys Met Glu Arg Val Ser Glu
95                  100                 105                 110 ccc tgc cca ggc tcc aag aag cag ctg aag ttt gaa gag ctc cag tgc     385
Pro Cys Pro Gly Ser Lys Lys Gln Leu Lys Phe Glu Glu Leu Gln Cys
                115                 120                 125 gac gtg tcc atg gag gag gac agc cgg cag gag tgg acc ttc acc ctg     433
Asp Val Ser Met Glu Glu Asp Ser Arg Gln Glu Trp Thr Phe Thr Leu
            130                 135                 140 tat gac ttt gac aac aac ggc aag gtc acc cga gag gac atc acc agc     481
Tyr Asp Phe Asp Asn Asn Gly Lys Val Thr Arg Glu Asp Ile Thr Ser
        145                 150                 155 ttg ctg cac acc atc tat gag gtg gtg gac tcc tct gtc aac cac tcc     529
Leu Leu His Thr Ile Tyr Glu Val Val Asp Ser Ser Val Asn His Ser
    160                 165                 170 cca aca tcc agc aag atg ctg cgg gta aag ctc acc gtg gcc ccc gat     577
Pro Thr Ser Ser Lys Met Leu Arg Val Lys Leu Thr Val Ala Pro Asp
175                 180                 185                 190 ggc agc cag agc aag agg agc gtc ctt gtc aat cag gct gac ctg cag     625
Gly Ser Gln Ser Lys Arg Ser Val Leu Val Asn Gln Ala Asp Leu Gln
                195                 200                 205 agc gca agg ccc cga gca gag acc aag ccc act gag gac ctg cgg agc     673
Ser Ala Arg Pro Arg Ala Glu Thr Lys Pro Thr Glu Asp Leu Arg Ser
            210                 215                 220 tgg gag aag aag cag cga gcc ccg ctc agg ttc cag ggt gac agc cgc     721
Trp Glu Lys Lys Gln Arg Ala Pro Leu Arg Phe Gln Gly Asp Ser Arg
        225                 230                 235 ctg gag cag tct ggc tgc tac cac cat tgc gta gat gag aac atc gag     769
Leu Glu Gln Ser Gly Cys Tyr His His Cys Val Asp Glu Asn Ile Glu
```

```
                Leu Glu Gln Ser Gly Cys Tyr His His Cys Val Asp Glu Asn Ile Glu
                    240                 245                 250 agg aga aac cac tac tta gat ctc gcc ggg ata gaa aac tac acg tcc      817
Arg Arg Asn His Tyr Leu Asp Leu Ala Gly Ile Glu Asn Tyr Thr Ser
255                 260                 265                 270 caa ttt ggg cct ggc tcc cct tcc gtg gcc cag aag tca gaa ctg ccc      865
Gln Phe Gly Pro Gly Ser Pro Ser Val Ala Gln Lys Ser Glu Leu Pro
                    275                 280                 285 ccc cgc acc ttc aat ccc act cga tct cgc tcc cat gag ccg gaa gcc      913
Pro Arg Thr Phe Asn Pro Thr Arg Ser Arg Ser His Glu Pro Glu Ala
                    290                 295                 300 atc cac atc cca cac cga aag ccc caa ggc gtg gac ccg gcc tcc ttc      961
Ile His Ile Pro His Arg Lys Pro Gln Gly Val Asp Pro Ala Ser Phe
                    305                 310                 315 cac ttc ctt gac acc cca atc gcc aag gtc tca gag ctc cag caa cgg     1009
His Phe Leu Asp Thr Pro Ile Ala Lys Val Ser Glu Leu Gln Gln Arg
320                 325                 330 ctc cgg ggc act cag gac ggg agc aag cac ttt gtg agg tcc ccc aag     1057
Leu Arg Gly Thr Gln Asp Gly Ser Lys His Phe Val Arg Ser Pro Lys
335                 340                 345                 350 gcc cag ggc aag agt gtg ggt gtg ggc cac gtg gcc aga ggg gca aga     1105
Ala Gln Gly Lys Ser Val Gly Val Gly His Val Ala Arg Gly Ala Arg
                    355                 360                 365 aac aag ccc cct ctg gga ccc gcc atc cct gcg gtg tcc ccc tcc gcc     1153
Asn Lys Pro Pro Leu Gly Pro Ala Ile Pro Ala Val Ser Pro Ser Ala
                    370                 375                 380 cac ctg gct gcc agc ccg gcc ctc ctc ccc tcc cta gcc ccc ctc ggg     1201
His Leu Ala Ala Ser Pro Ala Leu Leu Pro Ser Leu Ala Pro Leu Gly
                    385                 390                 395 cac aag aag cac aag cac cga gcc aag gag agc cag cag ggc tgc cgg     1249
His Lys Lys His Lys His Arg Ala Lys Glu Ser Gln Gln Gly Cys Arg
400                 405                 410 ggc ctg cag gca cca ctg gcc tca ggt ggc cct gtc ctg ggg cgg gag     1297
Gly Leu Gln Ala Pro Leu Ala Ser Gly Gly Pro Val Leu Gly Arg Glu
415                 420                 425                 430 cac ctg cgg gag ctg ccc gcc ttg gtg gtg tat gag agc cag gcc ggg     1345
His Leu Arg Glu Leu Pro Ala Leu Val Val Tyr Glu Ser Gln Ala Gly
                    435                 440                 445 cag ccg gtc cag aga cat gag cac cac cac cac cat gaa cat cac cac     1393
Gln Pro Val Gln Arg His Glu His His His His His Glu His His His
                    450                 455                 460 cat tac cac cac ttc tac cag aca t agagcccctc cccagggccc             1438
His Tyr His His Phe Tyr Gln Thr
                    465                 470

<210> SEQ ID NO 6
<211> LENGTH: 470
<212> TYPE: PRT
<213> ORGANISM: Homo sapiens

<400> SEQUENCE: 6

Met Gly Lys Leu His Ser Lys Pro Ala Ala Val Cys Lys Arg Arg Glu
 1               5                  10                  15

Ser Pro Glu Gly Asp Ser Phe Ala Val Ser Ala Ala Trp Ala Arg Lys
                20                  25                  30

Gly Ile Glu Glu Trp Ile Gly Arg Gln Arg Cys Pro Gly Gly Val Ser
            35                  40                  45

Gly Pro Arg Gln Leu Arg Leu Ala Gly Thr Ile Gly Arg Ser Thr Arg
        50                  55                  60
```

-continued

```
Glu Leu Val Gly Asp Val Leu Arg Asp Thr Leu Ser Glu Glu Glu Glu
 65                  70                  75                  80

Asp Asp Phe Arg Leu Glu Val Ala Leu Pro Pro Glu Lys Thr Asp Gly
             85                  90                  95

Leu Gly Ser Gly Asp Glu Lys Lys Met Glu Arg Val Ser Glu Pro Cys
            100                 105                 110

Pro Gly Ser Lys Lys Gln Leu Lys Phe Glu Glu Leu Gln Cys Asp Val
            115                 120                 125

Ser Met Glu Glu Asp Ser Arg Gln Glu Trp Thr Phe Thr Leu Tyr Asp
130                 135                 140

Phe Asp Asn Asn Gly Lys Val Thr Arg Glu Asp Ile Thr Ser Leu Leu
145                 150                 155                 160

His Thr Ile Tyr Glu Val Val Asp Ser Ser Val Asn His Ser Pro Thr
                165                 170                 175

Ser Ser Lys Met Leu Arg Val Lys Leu Thr Val Ala Pro Asp Gly Ser
            180                 185                 190

Gln Ser Lys Arg Ser Val Leu Val Asn Gln Ala Asp Leu Gln Ser Ala
            195                 200                 205

Arg Pro Arg Ala Glu Thr Lys Pro Thr Glu Asp Leu Arg Ser Trp Glu
            210                 215                 220

Lys Lys Gln Arg Ala Pro Leu Arg Phe Gln Gly Asp Ser Arg Leu Glu
225                 230                 235                 240

Gln Ser Gly Cys Tyr His His Cys Val Asp Glu Asn Ile Glu Arg Arg
                245                 250                 255

Asn His Tyr Leu Asp Leu Ala Gly Ile Glu Asn Tyr Thr Ser Gln Phe
            260                 265                 270

Gly Pro Gly Ser Pro Ser Val Ala Gln Lys Ser Glu Leu Pro Pro Arg
            275                 280                 285

Thr Phe Asn Pro Thr Arg Ser Arg Ser His Glu Pro Glu Ala Ile His
            290                 295                 300

Ile Pro His Arg Lys Pro Gln Gly Val Asp Pro Ala Ser Phe His Phe
305                 310                 315                 320

Leu Asp Thr Pro Ile Ala Lys Val Ser Glu Leu Gln Gln Arg Leu Arg
                325                 330                 335

Gly Thr Gln Asp Gly Ser Lys His Phe Val Arg Ser Pro Lys Ala Gln
            340                 345                 350

Gly Lys Ser Val Gly Val His Val Ala Arg Gly Ala Arg Asn Lys
            355                 360                 365

Pro Pro Leu Gly Pro Ala Ile Pro Ala Val Ser Pro Ser Ala His Leu
            370                 375                 380

Ala Ala Ser Pro Ala Leu Leu Pro Ser Leu Ala Pro Leu Gly His Lys
385                 390                 395                 400

Lys His Lys His Arg Ala Lys Glu Ser Gln Gln Gly Cys Arg Gly Leu
                405                 410                 415

Gln Ala Pro Leu Ala Ser Gly Gly Pro Val Leu Gly Arg Glu His Leu
            420                 425                 430

Arg Glu Leu Pro Ala Leu Val Val Tyr Glu Ser Gln Ala Gly Gln Pro
            435                 440                 445

Val Gln Arg His Glu His His His His Glu His His His His Tyr
            450                 455                 460

His His Phe Tyr Gln Thr
465                 470
```

-continued

```
<210> SEQ ID NO 7
<211> LENGTH: 1285
<212> TYPE: DNA
<213> ORGANISM: Mus musculus
<220> FEATURE:
<221> NAME/KEY: CDS
<222> LOCATION: (2)...(1282)
<223> OTHER INFORMATION: Nkd2 coding sequence

<400> SEQUENCE: 7
```

| | | | | | | | | | | | | | | | | |
|---|---|---|---|---|---|---|---|---|---|---|---|---|---|---|---|---|
| g | aat | tca | tgt | ctt | acg | gtc | aag | ggc | gcg | ggc | agc | ggc | gtg | gaa | cat | cgc | 49 |
| | Asn | Ser | Cys | Leu | Thr | Val | Lys | Gly | Ala | Gly | Ser | Gly | Val | Glu | His | Arg | |
| | 1 | | | 5 | | | | | 10 | | | | | 15 | | | |

| tca | cgg | gac | aag | cag | gag | ctg | ctc | aat | gga | gac | cct | aag | gag | ggg | cct | 97 |
|---|---|---|---|---|---|---|---|---|---|---|---|---|---|---|---|---|
| Ser | Arg | Asp | Lys | Gln | Glu | Leu | Leu | Asn | Gly | Asp | Pro | Lys | Glu | Gly | Pro | |
| | | 20 | | | | | 25 | | | | | 30 | | | | |

| ttc | tgg | gac | gac | aag | ggt | tcc | cta | gaa | gtt | gtg | ctg | ccc | cct | gag | aag | 145 |
|---|---|---|---|---|---|---|---|---|---|---|---|---|---|---|---|---|
| Phe | Trp | Asp | Asp | Lys | Gly | Ser | Leu | Glu | Val | Val | Leu | Pro | Pro | Glu | Lys | |
| | | | 35 | | | | | 40 | | | | | 45 | | | |

| tct | gag | ggc | cat | gag | ggc | cag | ggc | cag | ctc | ttc | agc | aca | gat | gat | ggg | 193 |
|---|---|---|---|---|---|---|---|---|---|---|---|---|---|---|---|---|
| Ser | Glu | Gly | His | Glu | Gly | Gln | Gly | Gln | Leu | Phe | Ser | Thr | Asp | Asp | Gly | |
| | 50 | | | | | 55 | | | | | 60 | | | | | |

| gag | aag | gca | gca | agc | cgt | gag | ggt | cca | ctg | aga | ctt | agc | aag | aag | cac | 241 |
|---|---|---|---|---|---|---|---|---|---|---|---|---|---|---|---|---|
| Glu | Lys | Ala | Ala | Ser | Arg | Glu | Gly | Pro | Leu | Arg | Leu | Ser | Lys | Lys | His | |
| 65 | | | | | 70 | | | | | 75 | | | | | 80 | |

| ttg | aac | att | gac | gca | ctg | cag | tgt | gac | gtc | tca | gtg | gaa | gaa | gac | aac | 289 |
|---|---|---|---|---|---|---|---|---|---|---|---|---|---|---|---|---|
| Leu | Asn | Ile | Asp | Ala | Leu | Gln | Cys | Asp | Val | Ser | Val | Glu | Glu | Asp | Asn | |
| | | | | 85 | | | | | 90 | | | | | 95 | | |

| cgc | caa | gaa | tgg | aca | ttc | aca | ttg | tat | gac | ttt | gac | aac | agt | ggg | aaa | 337 |
|---|---|---|---|---|---|---|---|---|---|---|---|---|---|---|---|---|
| Arg | Gln | Glu | Trp | Thr | Phe | Thr | Leu | Tyr | Asp | Phe | Asp | Asn | Ser | Gly | Lys | |
| | | | 100 | | | | | 105 | | | | | 110 | | | |

| gtc | acc | aga | gag | gac | atg | tcc | agc | ctg | atg | cac | acc | atc | tac | gag | gtt | 385 |
|---|---|---|---|---|---|---|---|---|---|---|---|---|---|---|---|---|
| Val | Thr | Arg | Glu | Asp | Met | Ser | Ser | Leu | Met | His | Thr | Ile | Tyr | Glu | Val | |
| | | 115 | | | | | 120 | | | | | 125 | | | | |

| gtc | gat | gcc | tct | gtc | aat | cac | tcc | tcc | ggc | agc | agc | aag | acc | ctt | cga | 433 |
|---|---|---|---|---|---|---|---|---|---|---|---|---|---|---|---|---|
| Val | Asp | Ala | Ser | Val | Asn | His | Ser | Ser | Gly | Ser | Ser | Lys | Thr | Leu | Arg | |
| | 130 | | | | | 135 | | | | | 140 | | | | | |

| gtg | aag | cta | act | gtc | agc | cct | gaa | ccc | tcc | agc | aag | aag | gaa | tgt | cct | 481 |
|---|---|---|---|---|---|---|---|---|---|---|---|---|---|---|---|---|
| Val | Lys | Leu | Thr | Val | Ser | Pro | Glu | Pro | Ser | Ser | Lys | Lys | Glu | Cys | Pro | |
| 145 | | | | | 150 | | | | | 155 | | | | | 160 | |

| ctc | act | ggc | caa | gac | cgg | gag | ccc | act | cgt | ggc | aga | aca | gag | att | gag | 529 |
|---|---|---|---|---|---|---|---|---|---|---|---|---|---|---|---|---|
| Leu | Thr | Gly | Gln | Asp | Arg | Glu | Pro | Thr | Arg | Gly | Arg | Thr | Glu | Ile | Glu | |
| | | | | 165 | | | | | 170 | | | | | 175 | | |

| ctc | aca | gat | gag | ccc | cga | gtg | gct | gac | aga | agg | cta | tcc | gcc | tac | agc | 577 |
|---|---|---|---|---|---|---|---|---|---|---|---|---|---|---|---|---|
| Leu | Thr | Asp | Glu | Pro | Arg | Val | Ala | Asp | Arg | Arg | Leu | Ser | Ala | Tyr | Ser | |
| | | | 180 | | | | | 185 | | | | | 190 | | | |

| agg | aag | ccc | aat | gct | gat | ccc | cag | ccc | tgc | tct | gtg | cga | gtg | ccc | tac | 625 |
|---|---|---|---|---|---|---|---|---|---|---|---|---|---|---|---|---|
| Arg | Lys | Pro | Asn | Ala | Asp | Pro | Gln | Pro | Cys | Ser | Val | Arg | Val | Pro | Tyr | |
| | | 195 | | | | | 200 | | | | | 205 | | | | |

| tgt | gtg | gat | gag | aac | aca | gag | cgc | aga | aac | cac | tac | cta | gac | ctt | gct | 673 |
|---|---|---|---|---|---|---|---|---|---|---|---|---|---|---|---|---|
| Cys | Val | Asp | Glu | Asn | Thr | Glu | Arg | Arg | Asn | His | Tyr | Leu | Asp | Leu | Ala | |
| | 210 | | | | | 215 | | | | | 220 | | | | | |

| ggc | atc | gag | aac | tac | aca | tct | aag | ttt | ggt | cct | ggg | tca | cca | cct | gag | 721 |
|---|---|---|---|---|---|---|---|---|---|---|---|---|---|---|---|---|
| Gly | Ile | Glu | Asn | Tyr | Thr | Ser | Lys | Phe | Gly | Pro | Gly | Ser | Pro | Pro | Glu | |
| 225 | | | | | 230 | | | | | 235 | | | | | 240 | |

| cag | gcc | agg | caa | gaa | cat | cat | ggc | agg | gcc | aca | cac | att | cca | agc | agg | 769 |
|---|---|---|---|---|---|---|---|---|---|---|---|---|---|---|---|---|
| Gln | Ala | Arg | Gln | Glu | His | His | Gly | Arg | Ala | Thr | His | Ile | Pro | Ser | Arg | |
| | | | | 245 | | | | | 250 | | | | | 255 | | |

| tcc | cga | tca | caa | gag | tcg | gat | gcc | cac | gct | ata | cac | cac | cgc | agg | tct | 817 |
|---|---|---|---|---|---|---|---|---|---|---|---|---|---|---|---|---|
| Ser | Arg | Ser | Gln | Glu | Ser | Asp | Ala | His | Ala | Ile | His | His | Arg | Arg | Ser | |
| | | | 260 | | | | | 265 | | | | | 270 | | | |

-continued

```
caa gtc ctg gct gag cat gtc ata cca gct aat gag cct gcc acc cgg         865
Gln Val Leu Ala Glu His Val Ile Pro Ala Asn Glu Pro Ala Thr Arg
        275                 280                 285 gcc ctg gct gca cag ccc cgg atc aag ggg cag gag aag cag ttc ctc         913
Ala Leu Ala Ala Gln Pro Arg Ile Lys Gly Gln Glu Lys Gln Phe Leu
290                 295                 300 agg tct cct aag ggt cca gga aaa cct ctt ggg aca cca ggc agt ggc         961
Arg Ser Pro Lys Gly Pro Gly Lys Pro Leu Gly Thr Pro Gly Ser Gly
305                 310                 315                 320 aag cca ggg aaa gct ctc agc tat tgc ctg cag gcc gtg cca ttg ccc        1009
Lys Pro Gly Lys Ala Leu Ser Tyr Cys Leu Gln Ala Val Pro Leu Pro
                325                 330                 335 cag agt gct cag gat ggc cac cac ctt cct cag ccc cca cag cct            1057
Gln Ser Ala Gln Asp Gly His His Leu Pro Gln Pro Pro Gln Pro
                340                 345                 350 cca ccg cag ccc tat ggt cac aag cgg tac cgg cag aaa gcc aga gaa        1105
Pro Pro Gln Pro Tyr Gly His Lys Arg Tyr Arg Gln Lys Ala Arg Glu
                355                 360                 365 ggc cac tca cca ctt aag ggg cat ggc cag cct acc atg gtg gag cat        1153
Gly His Ser Pro Leu Lys Gly His Gly Gln Pro Thr Met Val Glu His
370                 375                 380 gaa gta gta cgg gac ctg cct ccc atg ctg ggg cct gag ggc tat gtg        1201
Glu Val Val Arg Asp Leu Pro Pro Met Leu Gly Pro Glu Gly Tyr Val
385                 390                 395                 400 atg cct gtg gtc cag agg cat gaa cac cac cat cac cat gag cac cac        1249
Met Pro Val Val Gln Arg His Glu His His His His His Glu His His
                405                 410                 415 cac cat cac cac cac cac cag ttc cac cca tcc tag                        1285
His His His His His His Gln Phe His Pro Ser
                420                 425
```

<210> SEQ ID NO 8
<211> LENGTH: 427
<212> TYPE: PRT
<213> ORGANISM: Mus musculus

<400> SEQUENCE: 8

```
Asn Ser Cys Leu Thr Val Lys Gly Ala Gly Ser Gly Val Glu His Arg
 1               5                  10                  15

Ser Arg Asp Lys Gln Glu Leu Leu Asn Gly Asp Pro Lys Glu Gly Pro
                20                  25                  30

Phe Trp Asp Asp Lys Gly Ser Leu Glu Val Val Leu Pro Pro Glu Lys
            35                  40                  45

Ser Glu Gly His Glu Gly Gln Gly Gln Leu Phe Ser Thr Asp Asp Gly
        50                  55                  60

Glu Lys Ala Ala Ser Arg Glu Gly Pro Leu Arg Leu Ser Lys Lys His
65                  70                  75                  80

Leu Asn Ile Asp Ala Leu Gln Cys Asp Val Ser Val Glu Glu Asp Asn
                85                  90                  95

Arg Gln Glu Trp Thr Phe Thr Leu Tyr Asp Phe Asp Asn Ser Gly Lys
            100                 105                 110

Val Thr Arg Glu Asp Met Ser Ser Leu Met His Thr Ile Tyr Glu Val
        115                 120                 125

Val Asp Ala Ser Val Asn His Ser Ser Gly Ser Ser Lys Thr Leu Arg
    130                 135                 140

Val Lys Leu Thr Val Ser Pro Glu Pro Ser Ser Lys Lys Glu Cys Pro
145                 150                 155                 160

Leu Thr Gly Gln Asp Arg Glu Pro Thr Arg Gly Arg Thr Glu Ile Glu
```

```
                       165                 170                 175
        Leu Thr Asp Glu Pro Arg Val Ala Asp Arg Arg Leu Ser Ala Tyr Ser
                        180                 185                 190

Arg Lys Pro Asn Ala Asp Pro Gln Pro Cys Ser Val Arg Val Pro Tyr
                    195                 200                 205

Cys Val Asp Glu Asn Thr Glu Arg Arg Asn His Tyr Leu Asp Leu Ala
                210                 215                 220

Gly Ile Glu Asn Tyr Thr Ser Lys Phe Gly Pro Gly Ser Pro Pro Glu
        225                 230                 235                 240

Gln Ala Arg Gln Glu His His Gly Arg Ala Thr His Ile Pro Ser Arg
                        245                 250                 255

Ser Arg Ser Gln Glu Ser Asp Ala His Ala Ile His Arg Arg Ser
                    260                 265                 270

Gln Val Leu Ala Glu His Val Ile Pro Ala Asn Glu Pro Ala Thr Arg
                275                 280                 285

Ala Leu Ala Ala Gln Pro Arg Ile Lys Gly Gln Glu Lys Gln Phe Leu
        290                 295                 300

Arg Ser Pro Lys Gly Pro Lys Pro Leu Gly Thr Pro Gly Ser Gly
        305                 310                 315                 320

Lys Pro Gly Lys Ala Leu Ser Tyr Cys Leu Gln Ala Val Pro Leu Pro
                        325                 330                 335

Gln Ser Ala Gln Asp Gly His His Leu Pro Gln Pro Pro Gln Pro
                    340                 345                 350

Pro Pro Gln Pro Tyr Gly His Lys Arg Tyr Arg Gln Lys Ala Arg Glu
                355                 360                 365

Gly His Ser Pro Leu Lys Gly His Gly Gln Pro Thr Met Val Glu His
        370                 375                 380

Glu Val Val Arg Asp Leu Pro Pro Met Leu Gly Pro Glu Gly Tyr Val
        385                 390                 395                 400

Met Pro Val Val Gln Arg His Glu His His His His Glu His
                        405                 410                 415

His His His His His His Gln Phe His Pro Ser
                    420                 425

<210> SEQ ID NO 9
<211> LENGTH: 1307
<212> TYPE: DNA
<213> ORGANISM: Homo sapiens

<400> SEQUENCE: 9
gtggcggccg ctctagacta gtggatcccc cgggctgcag gaattcggca cgaggtcacc      60
agggaggaca tgtccagcct catgcacacc atctatgagg tcgtggatgc ctcggtcaac     120
cactcctcgg gcagcagcaa gaccctccgt gtgaagctaa ccgtcagccc tgagccctcc     180
agcaagagga aggagggtcc tcctgctggc caggaccggg agcccacccg ttgcaggatg     240
gagggtgaac tggcagagga gccaagggtg gctgacagga ggttgtctgc acacgtcagg     300
aggcccagta ctgaccccca gccctgctcg gagcggggc cctactgcgt ggacgagaac     360
acggagcgca gaaaccacta cctggacctc gccgggattg agaactacac gtccagattc     420
ggccctgggt cccctcctgt gcaagcaaag caggagcccc agggcagggc ctcgcacctc     480
caggcccggt cccgctccca ggagccagat acacatgccg taccaccccg caggtcacag     540
gtgctggtgg aacacgtcgt gccagcctcg agcctgctgc ccgggccct ggacacgcag     600 ccccggccga aggggccgga gaagcagttc ctcaagtccc caagggctc cgggaagccg     660
```

-continued

```
cctgggtgc cagccagcag caagtccggg aaagccttca gctactacct gccggccgtc    720
ctgccgcccc aggcccctca ggacggccac cacctcccgc agcccccacc gccaccctac    780
ggccacaagc ggtaccgcca aaagggcagg gagggccact cgccactcaa ggccccacac    840
gctcagcctg ccacagtgga gcacgaggtg gtgcgggacc tgccgcccac gccagcagga    900
gagggctacg cggtgccagt gatccagcgg cacgagcacc accaccacca cgagcaccac    960
caccaccacc accaccacca cttccacccg tcctagcgcc actgccaagc acacctcgct   1020
cccagcacac cacggcccgc gacctcaggg cagggagcag agcagctgcc ggctgtgtgc   1080
ccatggggag cccagccccc accccccacc tccgacagca aacagcaact gactgcaggt   1140
gctggcatga tggaggtggt gcaccttgga cacgtggaca aggcccaggc gccctctgct   1200
cttctgccct cgatgccaca tggcggtgaa cacatctgaa gccactatgt ttcctggctc   1260
taaggctcgt ctgtgtaacc cataaaacct gctttgattc caaaaaa              1307
```

<210> SEQ ID NO 10
<211> LENGTH: 399
<212> TYPE: PRT
<213> ORGANISM: Homo sapiens
<220> FEATURE:
<221> NAME/KEY: VARIANT
<222> LOCATION: (1)...(399)
<223> OTHER INFORMATION: Xaa = Any Amino Acid

<400> SEQUENCE: 10

```
Xaa Pro Lys Glu Gly Pro Phe Arg Glu Asp Gln Cys Pro Leu Gln Val
 1               5                  10                  15

Ala Leu Pro Ala Glu Lys Ala Glu Gly Arg Glu His Pro Gly Gln Leu
                20                  25                  30

Leu Ser Ala Asp Asp Gly Glu Arg Ala Ala Asn Arg Glu Gly Pro Arg
            35                  40                  45

Gly Pro Gly Gly Gln Arg Leu Asn Ile Asp Ala Leu Gln Cys Asp Val
        50                  55                  60

Ser Val Glu Glu Asp Asp Arg Gln Glu Trp Thr Phe Thr Leu Tyr Asp
65                  70                  75                  80

Phe Asn Asn Cys Gly Lys Val Thr Arg Glu Asp Met Ser Ser Leu Met
                85                  90                  95

His Thr Ile Tyr Glu Val Val Asp Ala Ser Val Asn His Ser Ser Gly
                100                 105                 110

Ser Ser Lys Thr Leu Arg Val Lys Leu Thr Val Ser Pro Glu Pro Ser
            115                 120                 125

Ser Lys Arg Lys Glu Gly Pro Pro Ala Gly Gln Asp Arg Glu Pro Thr
        130                 135                 140

Arg Cys Arg Met Glu Gly Glu Leu Ala Glu Pro Arg Val Ala Asp
145                 150                 155                 160

Arg Arg Leu Ser Ala His Val Arg Arg Pro Ser Thr Asp Pro Gln Pro
                165                 170                 175

Cys Ser Glu Arg Gly Pro Tyr Cys Val Asp Glu Asn Thr Glu Arg Arg
                180                 185                 190

Asn His Tyr Leu Asp Leu Ala Gly Ile Glu Asn Tyr Thr Ser Arg Phe
            195                 200                 205

Gly Pro Gly Ser Pro Pro Val Gln Ala Lys Gln Glu Pro Gln Gly Arg
        210                 215                 220

Ala Ser His Leu Gln Ala Arg Ser Arg Ser Gln Glu Pro Asp Thr His
225                 230                 235                 240
```

-continued

```
Ala Val His His Arg Arg Ser Gln Val Leu Val Glu His Val Val Pro
                245                 250                 255

Ala Ser Glu Pro Ala Ala Arg Ala Leu Asp Thr Gln Pro Arg Pro Lys
            260                 265                 270

Gly Pro Glu Lys Gln Phe Leu Lys Ser Pro Lys Gly Ser Gly Lys Pro
        275                 280                 285

Pro Gly Val Pro Ala Ser Ser Lys Ser Gly Lys Ala Phe Ser Tyr Tyr
    290                 295                 300

Leu Pro Ala Val Leu Pro Pro Gln Ala Pro Gln Asp Gly His His Leu
305                 310                 315                 320

Pro Gln Pro Pro Pro Pro Tyr Gly His Lys Arg Tyr Arg Gln Lys
                325                 330                 335

Gly Arg Glu Gly His Ser Pro Leu Lys Ala Pro His Ala Gln Pro Ala
            340                 345                 350

Thr Val Glu His Glu Val Val Arg Asp Leu Pro Pro Thr Pro Ala Gly
        355                 360                 365

Glu Gly Tyr Ala Val Pro Val Ile Gln Arg His Glu His His His
    370                 375                 380

His Glu His His His His His His His Phe His Pro Ser
385                 390                 395
```

<210> SEQ ID NO 11
<211> LENGTH: 18
<212> TYPE: DNA
<213> ORGANISM: Drosophila melanogaster

<400> SEQUENCE: 11
gctgctggtc agcgaacg                                                    18

<210> SEQ ID NO 12
<211> LENGTH: 19
<212> TYPE: DNA
<213> ORGANISM: Drosophila melanogaster

<400> SEQUENCE: 12
tgatgagact gctgcttac                                                   19

<210> SEQ ID NO 13
<211> LENGTH: 60
<212> TYPE: PRT
<213> ORGANISM: Drosophila melanogaster

<400> SEQUENCE: 13

```
Ile Arg Leu Glu Glu Phe Thr Cys Asp Val Ser Val Glu Gly Gly Lys
 1               5                  10                  15

Ser Ser Gln Pro Leu Gln Phe Ser Phe Thr Phe Tyr Asp Leu Asp Gly
            20                  25                  30

His His Gly Lys Ile Thr Lys Asp Asp Ile Val Gly Ile Val Tyr Thr
        35                  40                  45

Ile Tyr Glu Ser Ile Gly Lys Ser Val Val Val Pro
    50                  55                  60
```

<210> SEQ ID NO 14
<211> LENGTH: 60
<212> TYPE: PRT
<213> ORGANISM: Drosophila melanogaster

<400> SEQUENCE: 14

```
Ile Asp Phe Arg Glu Phe Leu Cys Ala Leu Ser Val Thr Ser Arg Gly
 1               5                  10                  15

Lys Leu Glu Gln Lys Leu Lys Trp Ala Phe Ser Met Tyr Asp Leu Asp
                20                  25                  30

Gly Asn Gly Tyr Ile Ser Arg Gln Glu Met Leu Glu Ile Val Thr Ala
                35                  40                  45

Ile Tyr Lys Met Val Gly Ser Val Met Lys Met Pro
        50                  55                  60

<210> SEQ ID NO 15
<211> LENGTH: 60
<212> TYPE: PRT
<213> ORGANISM: Bos Taurus

<400> SEQUENCE: 15

Leu Asp Phe Lys Glu Tyr Val Ile Ala Leu His Met Thr Ser Ala Gly
 1               5                  10                  15

Lys Thr Asn Gln Lys Leu Glu Trp Ala Phe Ser Leu Tyr Asp Val Asp
                20                  25                  30

Gly Asn Gly Thr Ile Ser Lys Asn Glu Val Leu Glu Ile Val Thr Ala
                35                  40                  45

Ile Phe Lys Met Ile Ser Pro Glu Asp Thr Lys His
        50                  55                  60
```

US 6,630,323 B1

NAKED CUTICLE GENES AND THEIR USES

CROSS-REFERENCE TO RELATED APPLICATIONS

This application claims the benefit of U.S. provisional application Serial No. 60/120,646, filed Feb. 17, 1999, which application is incorporated herein by reference.

This invention was made with support from the Howard Hughes Medical Institute. The Government may have certain rights in this invention.

BACKGROUND

Communication between cells is often mediated by secreted signaling molecules that bind cell surface receptors and modulate the activity of specific intracellular effectors. The Wnt family of secreted glycoproteins is one group of signaling molecules that has been shown to control a variety of developmental processes, including cell fate specification, cell proliferation, cell polarity and cell migration. In addition, mis-regulation of Wnt signaling can cause developmental defects and is implicated in the genesis of several human cancers. The Wnt growth factor family includes more than 10 genes identified in the mouse and at least 7 genes identified in the human.

Studies of mutations in Wnt genes have indicated a role for Wnts in growth control and tissue patterning. The Wnt-1 proto-oncogene (int-1) was originally identified from mammary tumors induced by mouse mammary tumor virus (MMTV) due to an insertion of viral DNA sequence. Knockout mutations in mice have shown Wnts to be essential for brain development, and the outgrowth of embryonic primordia for kidney, tail bud, and limb bud. Overexpression of Wnts in the mammary gland can result in mammary hyperplasia, and precocious alveolar development.

In Drosophila, Wingless signaling mediates endoderm induction and the establishment of segment polarity in the developing embryo. The fly Wingless cascade is strikingly similar to the vertebrate Wnt signaling pathway, which controls a number of key developmental decisions such as dorsal-ventral patterning in Xenopus.

The molecular mechanisms by which the Wnt signal regulates cellular functions are becoming increasingly well understood. Wnt stabilizes cytoplasmic beta-catenin, which stimulates the expression of genes including c-myc, c-jun, fra-1, and cyclin D1. Axin, newly recognized as a component of the Wnt signalling pathway, negatively regulates this pathway. Other components of the Wnt signalling pathway, including Dvl, glycogen synthase kinase-3beta, beta-catenin, and adenomatous polyposis coli, interact with Axin, and the phosphorylation and stability of beta-catenin are regulated in the Axin complex.

Recent findings suggest that Wnt signals can sometimes play a permissive role during cell-fate assignment. Wnt proteins have been shown to interact with a number of extracellular and cell-surface proteins, whereas many intracellular components of the Wnt-signalling pathway are also involved in other cellular functions. These observations suggest that the future understanding of Wnt signalling may require models that are based on a signalling network rather than a single linear pathway. Identification of the members of this network are of particular interest for their role in cellular differentation and growth.

Relevant Literature

The role of negative feedback mechanisms and their roles during pattern formation are discussed by Perrmon et al. (1999) Cell 97, 13–16.

The role of Wnt signaling in animal development is discussed by Cadigan & Nusse (1997) Genes Dev 11, 3286–3305. The effect of engrailed and hedgehog on wingless are discussed in Sanson et al. (1999) Cell 98, 207–216.

The patterning of the Drosophila embryonic epidermis, and the role onf wingless in epidermis patterning is discussed by DiNardo et al. (1994) Curr Opin Genet Dev 4, 529–534; and Bejsovec & Martinez (1991) Development 113, 471–485. Pazdera et al. (1998) Development 125, 3427–3436 disclose patterned epidermal cell death in wild-type and segment polarity mutant Drosophila embryos. Moline et al. (1999) Development 126, 4375–4384 show that directionality of Wingless protein transport influences epidermal patterning in the Drosophila embryo.

SUMMARY OF THE INVENTION

Isolated nucleotide compositions and sequences are provided for naked cuticle (nkd) genes. The nkd nucleic acid compositions find use in identifying homologous or related genes; in producing compositions that modulate the expression or function of its encoded protein, Nkd; for gene therapy; mapping functional regions of the protein; and in studying associated physiological pathways. In addition, modulation of the gene activity in vivo is used for prophylactic and therapeutic purposes, such as treatment of cancer, identification of cell type based on expression, and the like.

The segment-polarity gene, naked cuticle (nkd), is shown to limit the effects of Wnt signaling. nkd expression can be inducible by Wnt signaling. nkd encodes a novel protein with a single EF-hand most similar to the recoverin family of myristoyl switch proteins and may link ion fluxes to the regulation of Wnt signal potency, duration, or distribution. Nkd proteins may restrain responses to Wnt proteins in their many roles in vertebrate development and disease.

BRIEF DESCRIPTION OF THE DRAWINGS

FIGS. 1a to 1i show nkd embryonic phenotype & rescue by nkd cDNA.

FIGS. 2a to 2d show diagrams of the sequence and genomic organization of the nkd gene.

FIGS. 3a to 3d show nkd expression and dependence on wg.

FIGS. 4a to 4m illustrate the consequences of altered levels of nkd activity.

FIGS. 5a to 5h show the effects of misexpression of fly Nkd in Xenopus embryos and animal caps.

DESCRIPTION OF THE SPECIFIC EMBODIMENTS

Nucleic acid compositions encoding naked cuticle (nkd) are provided. They are used in identifying homologous or related genes; in producing compositions that modulate the expression or function of its encoded protein; for gene therapy; mapping functional regions of the protein; and in studying associated physiological pathways.

Characterization of NKD

Nkd is widely expressed, typically in cells that also express Wg/Wnt. The Drosophila gene sequence is provided as SEQ ID NO:1, the encoded polypeptide product as SEQ ID NO:2. The gene product acts to antagonize Wnt signalling. Related human genetic sequences are provided as SEQ ID NO:5 and SEQ ID NO:9, with the corresponding polypeptides provided as SEQ ID NO:6 and SEQ ID NO:10. The related mouse genetic sequences are provided as SEQ ID NO:3 and SEQ ID NO:7, with the corresponding polypeptides provided as SEQ ID NO:4 and SEQ ID NO:8.

nkd encodes a novel protein with a single EF-hand most similar to the recoverin family of myristoyl switch proteins. Nkd may therefore link ion fluxes to the regulation of Wnt signal potency, duration, or distribution. Signal-inducible feedback antagonists like nkd may restrain the effects of Wnt proteins in development and disease. Antagonist gene dosage must be carefully regulated in flies and vertebrates to balance the effects of the signals. In Drosophila, nkd and ptc mutations have haploinsufficient effects on cuticle pattern in combination with each other and with other segment polarity mutants. Altered regulation of both Wnt and Hh signalling in mice and humans is implicated in precancerous and cancerous cell growth. Just as vertebrate ptc1 regulates cell fates and is a key tumor suppressor gene, vertebrate Nkd-like proteins may be essential for restraining Wnt activity during development and possibly cancer progression.

Homologs of nkd are identified by any of a number of methods. For example, a fragment of the Drosophila cDNA may be used as a hybridization probe against a cDNA library from the target organism of interest, where low stringency conditions are used. The probe may be a large fragment, or one or more short degenerate primers. Such sequences are selected from regions that are not likely to diverge over evolutionary time and are of low degeneracy. The complementary binding sequence will usually be at least 14 nucleotides, preferably at least about 17 nucleotides and usually not more than about 30 nucleotides. Conveniently, amplification reactions are used to generate an initial probe, which can then be used to hybridize to a library; for rapid amplification of cloned ends (RACE); etc. One or more of the resulting clones may then be used to rescreen the library to obtain an extended sequence, up to and including the entire coding region, as well as the non-coding 5'- and 3'-sequences. As appropriate, one may sequence all or a portion of the resulting cDNA coding sequence. The source of MRNA for a cDNA library will use cells where naked is known to be expressed, for example embryonic limb bud tissue.

Nucleic acids having sequence similarity to the provided nkd genetic sequences are detected by hybridization under low stringency conditions, for example, at 50° C. and 6×SSC (0.9 M NaCl/0.09 M Na citrate) and remain bound when subjected to washing at 55° C. in 1×SSC (0.15 M NaCl/0.015 M Na citrate). Sequence identity may be determined by hybridization under stringent conditions, for example, at 50° C. or higher and 0.1×SSC (15 mM NaCl/01.5 mM Na citrate). Nucleic acids having a region of substantial identity to the provided nkd sequences, e.g. allelic variants, genetically altered versions of the gene, etc., bind to the provided nkd sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between species in a group, e.g. human and mouse, homologs have substantial sequence similarity, i.e. at least 75% sequence identity between nucleotide sequences, in some cases 80 or 90% sequence identity, and may be as high as 95% sequence identity between closely related species. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), J. Mol. Biol. 215:403–10. In general, variants of the invention have a sequence identity greater than at least about 65%, preferably at least about 75%, more preferably at least about 85%, and may be greater than at least about 90% or more as determined by the Smith-Waterman homology search algorithm as implemented in MPSRCH program (Oxford Molecular). Exemplary search parameters for use with the MPSRCH program in order to identify sequences of a desired sequence identity are as follows: gap open penalty: 12; and gap extension penalty: 1.

NKD Nucleic Acid Compositions

Nucleic acids encoding nkd may be cDNA or genomic DNA or a fragment thereof. The term "nkd gene" shall be intended to mean the open reading frame encoding specific nkd polypeptides, introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a Nkd protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where nkd is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626.

The regulatory sequences may be used to identify cis acting sequences required for transcriptional or translational regulation of nkd expression, especially in different tissues or stages of development, and to identify cis acting sequences and trans acting factors that regulate or mediate nkd expression. Such transcription or translational control regions may be operably linked to a nkd gene in order to promote expression of wild type or altered nkd or other proteins of interest in cultured cells, or in embryonic, fetal or adult tissues, and for gene therapy.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening probes, etc. Larger DNA fragments, i.e. greater than 100 or 250 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The nkd genes are isolated and obtained in substantial purity, generally as other than an intact, naturally occurring chromosome. Usually, the DNA will be obtained substantially free of other nucleic acid sequences that do not include a nkd sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of nkd gene expression in the sample.

The sequence of a nkd gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989). Such mutated genes may be used to study structure-function relationships of nkd, or to alter properties of the protein that affect its function or regulation.

NKD Polypeptides

The subject gene may be employed for producing all or portions of Nkd polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a nkd gene, or may be derived from exogenous sources.

The peptide may be expressed in pro karyotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the nkd gene in eukaryotic cells, where the Nkd protein will benefit from native folding and post-translational modifications. Small peptides can also be synthesized in the laboratory. Peptides that are subsets of the complete nkd sequence, e.g. peptides of at least about 8 amino acids in length, usually at least about 12 amino acids in length, and may be as many as about 20 amino acids in length, up to substantially the length of the intact protein, may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed Nkd polypeptides are used for the production of antibodies, where short fragments provide for antibodies specific for the particular polypeptide, and larger fragments or the entire protein allow for the production of antibodies over the surface of the polypeptide. Antibodies may be raised to the wild-type or variant forms of Nkd. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y. 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Diagnostic Uses

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in a nkd coding region or control regions is associated with disease. Disease associated polymorphisms may include mutations that alter expression level, that affect protein function, etc.

Changes in the promoter or enhancer sequence that may affect expression levels of nkd can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express nkd may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine(TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type nkd sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in nkd may be based on the functional or antigenic characteristics of the protein. Protein truncation assays are useful in detecting deletions that may affect the biological activity of the protein. Various immunoassays designed to detect polymorphisms in Nkd proteins may be used in screening. Where many diverse genetic mutations lead to a particular disease phenotype, functional protein assays have proven to be effective screening tools. The activity of the encoded Nkd protein in regulation of Wnt may be determined by comparison with the wild-type protein.

Antibodies specific for a Nkd polypeptide may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal Nkd in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Modulation of Gene Expression

The nkd genes, gene fragments, or the encoded protein or protein fragments are useful in gene therapy to treat disorders associated with nkd defects. Expression vectors may be used to introduce the nkd gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or Nkd protein may be introduced into tissues or host cells by any number of routes, including viral infection, microinjection, or fusion of vesicles. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold microprojectiles are coated with the Nkd protein or DNA, then bombarded into skin cells.

Antisense molecules can be used to down-regulate expression of nkd in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur, phosphoroamidites; alkyl phosphotriesters and boranophosphates. Achiral phosphate derivatives include 3'-O'-5'-S-phosphorothioate,3'-S-5'-O-phosphorothioate,3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expressions vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

Genetically Altered Cell or Animal Models for Naked Cuticle Function

The subject nucleic acids can be used to generate transgenic animals or site specific gene modifications in cell lines. Transgenic animals may be made through homologous recombination, where the normal naked cuticle locus is altered. Alternatively, a nucleic acid construct is randomly integrated into the genome. Vectors for stable integration include plasmids, retroviruses and other animal viruses, YACs, and the like.

The modified cells or animals are useful in the study of naked cuticle function and regulation. For example, a series of small deletions and/or substitutions may be made in the naked cuticle gene to determine the role of different exons in oncogenesis, signal transduction, etc. Of interest are the use of nkd to construct transgenic animal models for cancer, where expression of nkd is specifically reduced or absent, e.g. in skin cells, brain cells, etc. Specific constructs of interest include anti-sense nkd, which will block nkd expression, expression of dominant negative nkd mutations, and over-expression of Wnt genes. A detectable marker, such as lac Z may be introduced into the naked cuticle locus, where upregulation of naked cuticle expression will result in an easily detected change in phenotype.

One may also provide for expression of the naked cuticle gene or variants thereof in cells or tissues where it is not normally expressed or at abnormal times of development. In addition, by providing expression of Nkd protein in cells in which it is not normally produced, one can induce changes in cell behavior, e.g. through nkd mediated signaling modulation.

DNA constructs for homologous recombination will comprise at least a portion of the naked cuticle gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keyed et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells. are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on GLI transcriptional activation, developmental abnormalities, etc.

In Vitro Models for Naked Cuticle Function

The availability of a number of components in the wnt signaling pathway allows in vitro reconstruction of the pathway. Two or more of the components may be combined in vitro, and the behavior assessed in terms of Wnt-dependent transcriptional activation; modification of protein components, e.g. proteolytic processing, phosphorylation, methylation, etc.; ability of different protein components to bind to each other, etc. The components may be modified by sequence deletion, substitution, etc. to determine the functional role of specific domains.

Drug screening may be performed using an in vitro model, a genetically altered cell or animal, or purified naked cuticle protein. One can identify ligands or substrates that bind to, modulate or mimic the action of naked cuticle. Areas of investigation include the development of cancer treatments, adverse effects of aging, metastasis, etc.

Drug screening identifies agents that provide a replacement for Nkd function in abnormal cells. Agents that mimic its function are predicted to inhibit the process of oncogenesis. Conversely, agents that reverse Nkd function may stimulate controlled growth and healing. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions.

The term "agent" as used herein describes any molecule, e.g. protein or pharmaceutical, with the capability of altering or mimicking the physiological function of naked cuticle. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic naked cuticle function. The level of naked cuticle activity is determined by a functional assay, as previously described. In one screening assay, candidate agents are added in combination with Wnt protein, and the ability to limit wnt signalling is detected. Alternatively, candidate agents are added to a cell that lacks functional Nkd, and screened for the ability to reproduce Nkd in a functional assay.

The compounds having the desired pharmacological activity may be administered in a physiologically acceptable carrier to a host for treatment of cancer, developmental abnormalities attributable to a defect in naked cuticle function, etc. The compounds may also be used to enhance naked cuticle function in wound healing, aging, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Naked Cuticle Encodes an Inducible Feedback Antagonist of Wingless/Wnt Activity

Animal development requires that cells respond appropriately to localized secreted signals. Proper responses to Hedgehog, TGFβ, EGF, and FGF/ras signals require cognate inducible antagonists such as Patched, Dad, Argos, and Sprouty (Perrimon et al. (1999) Cell 97:13–16). Wnt signals play crucial roles in development and neoplasia (Cadigan & Nusse (1997) Genes Dev 11:3286–3305).

Here we show that naked cuticle (nkd), a Drosophila segment polarity gene, encodes a novel inducible antagonist for the Wnt signal Wingless (Wg). In fly embryos and imaginal discs nkd transcription is inducible by Wg. In embryos, decreased nkd function has an effect similar to excess Wg; reduction of postembryonic nkd function is without apparent consequence. Conversely, Nkd overproduction in Drosophila, and misexpression in the vertebrate *Xenopus laevis*, results in phenotypes resembling Wg/Wnt loss of function.

Wg is critical for patterning events during the three stages of Drosophila embryonic segmentation (DiNardo et al. (1994) *Curr Opin Genet Dev* 4:529–534). First, between 3–3.5 hr. after egg laying (AEL), adjacent stripes of cells produce Wg and Hedgehog (Hh); Engrailed (En) and Hh are co-expressed. Second, between 3.5 and 6 hr. AEL, Wg maintains hh/en transcription, and Hh maintains wg transcription, producing a transient segmentation landmark, the parasegmental groove. Finally, 6 hr AEL and thereafter, definitive segmentation results in ventral epidermal cells synthesizing a segmentally repeated trapezoidal array of six unique types of cell protrusions called denticles, interspersed with naked (denticle-free) cuticle. During this stage, Wg specifies naked cuticle fates (Bejsovec et al. (1991) *Development* 113:471–485; Sanson et al. (1999) *Cell* 98:207–216).

nkd is an embryonic lethal recessive zygotic mutation with multiple segmentation defects. The most prominent defect is the replacement of denticles by excess naked cuticle (Jürgens et al. (1984) *Wilhelm Roux Arch Devl Biol* 193:283–295). FIG. 1*a* shows wild type ventral cuticle; FIG. 1*b* shows stage 11 embryonic En stains; FIG. 1*c* shows Wg stains. Homozygous strong nkd mutants ($nkd^{7H16}$ or $nkd^{7E89}$) display excess naked cuticle (FIG. 1*d*), have widened En (FIG. 1*e*) staining (black arrowheads), and normally spaced endogenous wg (FIG. 1*f*) stripes (black arrows) interspersed with ectopic wg stripes (red arrows) most commonly in alternate parasegments. Ubiquitous Nkd expression in homozygous $nkd^{7H16}$ or $nkd^{7E89}$ embryos rescues the naked cuticle phenotype (FIG. 1*g*), narrows En stripes to 2–3 cells wide (FIG. 1*h*), and restores the wild-type Wg expression pattern (FIG. 1*i*). Homozygous mutant nkd embryos are identified by absence of hunchback-lacZ expression (red arrowheads) on the TM3 balancer chromosome. The most potent rescue was observed when a 2–4 hr collection of P[Hs-nkd]; $nkd^{7H16}$/TM3 was heat shocked for 15 minutes at 37° C., which resulted in 0% "strong" cuticles, 12% "moderate" cuticles, 12% "weak" cuticles, and 76% wild type cuticles (n=101) (see Methods for cuticle scoring). Scale bar=60 μm.

This phenotype also seen in embryos exposed to excess Wg, as well as in embryos lacking both maternal and zygotic contributions from any of three genes which antagonize Wg: zeste-white3/glycogen synthase kinase 3β (zw3/gsk3β), D-axin, and D-Apc2. In nkd embryos, hh and en transcripts initiate normally but accumulate in broad stripes including cells further from the source of Wg, as if those cells are hypersensitive to Wg (FIG. 1*e*). Next, a stripe of new wg transcription appears just posterior to the expanded Hh/En stripe (FIG. 1*f*). This extra wg stripe requires both wg and hh activity and is required for the excess naked cuticle seen in nkd mutants (Dougan et al. (1992) *Nature* 360:347–350). Cell death in Hh/En-expressing cells contributes to the marked shortening of nkd mutant cuticles (FIG. 1d); (Pazdera et al. (1998) *Development* 125:3427–3436).

To clone nkd, we identified a fly stock with a lacZ P-element insertion in the nkd gene. DNA adjacent to the P insert was used to probe cDNA and genomic libraries, resulting in an approximately 80 kb genomic DNA walk (FIG. 2a). FIG. 2a shows a genomic map of nkd relative to centromere (cen) and telomere (tel) of chromosome 3L, band 75F. P element transposon I(3)4869 is upstream of exon 1. nkd has 5 exons (numbered 1–5) with a ~25 kb first intron. The putative initiator methionine (M) is near the 3' end of the first exon, while the stop codon (X) is in the middle of exon 5. A nonsense mutation at codon 60 (arrow above exon 2) was found in nkd$^{7H16}$.

A single 5 kb mRNA transcript derived from 40 kb of genomic DNA is expressed zygotically in a striped pattern (FIGS. 2a, b and 3). FIG. 2b is a developmental embryonic northern blot. Hours AEL are designated above each lane. FIG. 2c shows an immunoprecipitation of Nkd from 3–8 hr. embryonic extracts by anti-Nkd antibody. P—preimmune antisera; I—immune affinity purified anti-Nkd antisera; S—supernatant; P—pellet. A specific band (arrow) migrates above the 120 kDa marker. Consistent with the lack of a maternal requirement for nkd, the transcript is absent from 0–2 hr, maternally derived embryonic RNA. The longest cDNA, 4954 bp, has an open reading frame (ORF) of 2784 bp, encoding a 928 amino acid relatively basic (pl=9.1) and largely hydrophilic protein. Single-stranded conformation polymorphism (SSCP) analysis and direct genomic sequencing reveals a nonsense mutation Q60stop in nkd$^{7H16}$, predicting a truncated protein of 59 amino acids (FIG. 2a). The identity of the nkd cDNA was further confirmed by its ability, when activated with a heat shock promoter, to rescue the naked cuticle phenotype and the En and Wg expression abnormalities in nkd mutants (FIGS. 1g–i).

Nkd has significant similarity to the high affinity $Ca^{2+}$-binding EF hand of the recoverin family of myristoyl switch proteins (FIG. 2d; 39% amino acid identity, 63% similarity with Drosophila neurocalcin, p=$5 \times 10^{-6}$). FIG. 2d is an alignment of EF-hand similarity between Nkd and third EF hand in recoverin family of proteins. Amino acid identities between Drosophila Nkd (Dm. Nkd), Drosophila Neurocalcin (Dm. Ncalc) (Genbank accession #1171668), and bovine Recoverin (Bov. Rec)(Genbank accession #494545) are designated by vertical bars. Consensus EF hand residues (EF cons) are shown in key symbols used by Stryer (above) or Kretsinger (below). Key: h—hydrophobic residue; E—acidic residue, usually glutamic acid; O—oxygen donating residue which binds $Ca^{2+}$; G—glycine; *—variable amino acid; J—hydrophobic residue; X, Y, Z—coordinates of $Ca^{2+}$ binding in 3D space. EF hands are conserved $Ca^{2+}$-binding motifs that usually occur in pairs, although they have been observed singly. Mouse and human cDNA clones encoding EF-hand sequences similar to fly Nkd are provided as SEQ ID NO:3–10.

Affinity purified anti-Nkd antisera made against either of two parts of the protein detect a segmentally repeated cytoplasmic distribution very similar to the embryonic RNA pattern (FIGS. 3a,b). No staining is detected in nkd$^{7H16}$ mutant embryos, and high-level ubiqitous expression is seen in heat shocked P[Hs-nkd] embryos (FIG. 3b). Nkd antibody immunoprecipitates from embryonic protein extracts a protein that runs at a slightly higher molecular weight than the predicted size of 102 kD (FIG. 2c).

nkd transcription initiates in embryos during the late cellular blastoderm stage in broad anterior and posterior domains reminiscent of gap genes (FIG. 3a, stage 6). FIG. 3a shows nkd expression during embryonic stages 6–7 (left), 9 (middle), and 11 (right); anterior is left in all panels. St. 6 nkd RNA (top) and Nkd protein (α-Nkd; middle) patterns are similar. Embryo labelled for En protein (brown) and nkd RNA (purple) is shown (bottom). Stages 9 and 11: nkd RNA +/−En protein patterns at low (top row) and higher power (bottom two rows). nkd accumulates posterior to the Hh/En stripe during st. 9 (red bracket). Later (st. 11), nkd RNA is highest in the 2–3 cell rows anterior to the Hh/En stripe (white bracket), while at lower levels just posterior to the En stripe (red bracket). Parasegmental grooves are marked with red arrowheads in a and c.

During early germ band extension (stage 8–9), nkd transcription is nearly ubiquitous, with higher.RNA levels precisely in the 2–3 cell rows posterior to the Hh/En stripe that require nkd to limit Hh/En expression (FIG. 3a, stage 9). At this stage, Wg protein is evenly distributed on both sides of the stripe of cells that produce wg RNA. During full germ band extension, nkd expression is most abundant anterior to, and lower just posterior to, the Hh/En stripe (FIG. 3a, stage 10–11). Still lower nkd RNA is detectable in the Hh/En-expressing cells. Hh signalling in the Hh/En cells excludes Wg protein during this time, resulting in asymmetric Wg distribution with an anterior bias. nkd mutants do not develop this anterior bias of Wg protein (Moline et al. (1999) *Development* 126:4375–4384), suggesting nkd may be required for hh to exclude Wg protein from Hh/En cells. Nonetheless, after embryonic stage 10, Wg protein and nkd RNA are coincident in multiple tissues. nkd RNA and wg RNA are produced in overlapping patterns in imaginal discs and other larval tissues as well, with nkd domains slightly broader than wg (FIG. 3d).

We tested the possibility that nkd is regulated by Wg activity using gain and loss of function experiments. In wg mutant embryos, nkd transcription initiates normally but is markedly reduced by stage 11 (FIG. 3c). nkd transcript accumulates to higher levels in nkd mutant embryos (FIG. 3c), presumably due to the lack of negative feedback that Nkd protein normally provides to its own Wg-dependent expression. Enhanced nkd expression is seen when Wg is ubiquitously expressed in the embryo. Misexpression of either Wg or an activated form of the wg-signal transducer Armadillo (UAS-Arm$^{S10}$). in wing, leg, haltere, and antennal imaginal discs results in similar patterns of ectopic nkd transcription (FIG. 3d). Arm$^{S10}$-induced nkd transcript obeys sharp boundaries consistent with a cell autonomous nkd induction by Wg.

FIG. 3b shows that α-Nkd antisera does not stain nkd$^{7H16}$ embryos (left) and stains all cells after P[Hs-nkd] embryos are briefly heat pulsed at 37° C. (center left). Wild type st. 7 (center right) and 11 (right) embryos stained with α-Nkd antisera reveal cytoplasmic and plasma membrane associated (inset, arrowheads) epidermal staining similar to the RNA pattern. *—nucleus; brackets as in a. FIG. 3c shows nkd in situ hybridization to st. 11 wild type (+), wg (middle) and nkd (right) mutant embryos. FIG. 3d illustrates regulation of nkd expression by wg in third instar wing pouch (left panels) and leg (right panels) imaginal discs. Top row: wg RNA defines the presumptive wing margin and ventral-anterior sector of the leg disc (blue arrowheads). Middle row: nkd (red arrowheads) is broader than wg. Bottom row: Ectopic nkd (red arrows) accumulates perpendicular to wing margin or in the dorsal leg disc when dpp-Gal4. transgene drives UAS-wg. Scale bar=85 μm in left and upper panels of 3a, left two panels of 3b, and 3c; 35 μm for right and lower panels of 3a, right panels of 3b, and left panels of 3d; 7 μm for the right center panel inset of 3b; and 70 μm for the right panels of 3d.

If loss of hkd mimics the effect of excess Wg, then excess Nkd should mimic loss of wg. When P[Hs-nkd] is used to overexpress nkd in otherwise wild-type embryos, rare cuticles with weak wg-like denticle fusion phenotypes are observed (not shown), similar to those seen when zw3 is overexpressed. Nkd is more potent in a sensitized wg/+ background. In wg$^{H114}$/+ embryos, induction of P[Hs-nkd] prior to 4 h AEL results in decreased en and wg expression. wg$^{H114}$/+ embryos are normally patterned, but practically all wg$^{H114}$/+ embryos exposed to high levels of Nkd secrete cuticles with denticle belt fusions and an excess of the predominant denticle type made by wg/wg embryos (FIGS. 4a, b).

Misexpressing nkd during larval development with UAS/Gal4 transgenes results in adult phenotypes indistinguishable from many wg loss of function phenotypes. Phenotypes we observed include 1) wing to notum transformations; 2) leg truncations (FIG. 4e) and duplications (FIG. 4f); 3) loss, lateral displacement, and disorientation of sternite bristles; 4) haltere loss; 5) ventral eye reduction; 6) loss of wing margin; 7) extra wing anterior crossveins, and 8) loss of antennae. Wg-pathway gene dosage influences the effect of ectopic Nkd: loss of one wild-type copy of porcupine (porc), wg, dishevelled (dsh), or arm enhances, while zw3 and nkd suppress, the UAS-nkd overexpression phenotypes.

FIG. 4a shows ubiquitous Nkd expression using P[Hs-nkd] in wg/+ embryos before 4 hr AEL results in shortened embryos (left, darkfield) with denticle fusions and excess type 5 denticles (right, and magnified inset). FIG. 4b, wg/wg mutant embryos display a uniform lawn of type 5 denticles, and are unaffected by excess nkd. FIG. 4c, X-gal stained dpp-lacZ leg disc. dpp is expressed along the A–P axis at high levels dorsally (red arrow) and lower levels ventrally (black arrow). FIG. 4d, E105-Gal4; UAS-nkd imaginal discs have equally high levels of dpp-lacZ expression dorsally and ventrally (red arrows). FIG. 4e, E105-Gal4; UAS-nkd legs are variably truncated. FIG. 4f, B119-Gal4;UAS-nkd legs are variably duplicated. FIGS. 4g,h, Phenotypically normal nkd$^{7E89}$ mutant wing margin (g) and leg clone (h) marked with the bristle marker yellow. Scale bar=110 μm for the left images of 4a, b; 40 μm for 4c, d; 120 μm for 4e–h; 35 μm for k–m.

During leg development, Wg and Decapentaplegic (Dpp; a BMP-related signalling protein) act as mutually antagonistic determinants of dorsal and ventral identity. Dpp is expressed at high levels at the anterior-posterior (A-P) boundary dorsally, and at lower levels ventrally (FIG. 4c). Wg/Dpp juxtaposition results in leg disc eversion and outgrowth during pupal morphogenesis. Excess Nkd expressed throughout the disc results in high levels of dpp-lacZ expression along the entire A-P border of the disc (FIG. 4d), and scant wg-lacZ expression, similar to what is seen when wg activity is reduced. These discs give rise to variably truncated legs (FIG. 4e), indicating that excess Nkd can antagonize the normal effects of wg. More restricted ventral Nkd misexpression results in duplicated legs (FIG. 4f), which may arise by an abnormal juxtaposition of cells still expressing Wg to cells in which excess Nkd results in decreased Wg, and hence derepressed dpp. Thus two Wg/Dpp boundaries are created, and duplicated appendages result.

We induced nkd loss of function clones in imaginal discs and adult structures using two strong nkd alleles, nkd$^{7H16}$ and nkd$^{7E89}$, and one moderately severe allele, nkd$^{9G33}$, all of which are embryonic lethal. nkd alleles were originally generated in the genetic background of a weak allele of the pair-rule gene hairy (h$^1$). h$^1$ clones give rise to ectopic wing vein bristles and thoracic microchaetes. Further, nkd and h genetically interact: nkd, h$^1$/h$^{null}$ is lethal, while h$^1$/h$^{null}$ is viable. Therefore we also generated clones of the strong allele nkd$^{7E89}$ from which h$^1$ had been removed. In many tissues where Wg signals control pattern, including the wing (FIG. 4g), leg (FIG. 4h), thorax, abdomen, haltere, and eye, we observed phenotypically normal nkd clones. h$^1$, nkd$^{7H16}$, but not h$^+$, nkd$^{7E89}$ or h$^1$, nkd$^{9G33}$ clones give rise to a rough eye phenotype and loss of wing margin bristle phenotype which may be due to h/nkd interactions.

To test whether nkd clones arise at biased locations, we scored clones in adult legs marked with the bristle marker yellow (FIGS. 4i, j). nkd and control clones appeared with similar frequency in each leg quadrant (FIG. 4i). We assayed the expression of Wg target genes in nkd clones to look for subtle changes in gene expression that might be compatible with normal tissue patterning. Distalless (Dll) is distributed in a broad gradient centered on the wing disc margin (FIG. 4k). Induction of nkd clones results in no apparent alteration in the Dll expression gradient within, or adjacent to, multiple clones (FIGS. 4k–m). No changes in cytoplasmic Arm accumulation, an indicator of Wg activity, are noted within or adjacent to nkd clones.

FIG. 4i, Leg disc fate map schematic with sectors of unique bristle identities labelled as follows: green (anterior+anterior dorsal), blue (dorsal+posterior dorsal), lavender (posterior+posterior ventral), yellow (ventral+anterior ventral). Bristles in tibial and tarsal leg segments were scored. Perimeter of approximate domains of Wg (red) and nkd (blue) expression are designated with lines. FIG. 4j is a bar graph showing % of nkd$^{7E89}$ clones (n=39; colored bars) and control clones (n=28; black bars) as a function of leg disc quadrant as shown in i. Note that within each sector, nkd and control clones occur with comparable frequency. FIGS. 4k–m, Negative (k,l) and positive (m) confocal images of horizontally oriented wing disc margin primordia harboring multiple nkd$^{9G33}$ clones (marked by lack of P-myc stain in l; green in merged image of m) stained with anti-Dll (k, red in m). Representative clone spanning region of greatest drop-off in Dll stain is noted by a yellow line around its perimeter, highlighted by arrows in k. Twin spots are marked by more intense P-myc stain throughout the disc (l,m).

We then asked whether fly nkd can alter Wnt signalling in a vertebrate by using mRNA injection into *Xenopus laevis* embryos. Dorsal blastomere injection of RNAs encoding Wnt antagonists FrzB, as well as dominant inhibitory forms of Xfrizzled 8 (NXfz8)(FIG. 5b), Dishevelled (Xdd), and Wnt-8 (DN-Xwnt-8) into 4 cell embryos results in marked A-P axis truncations. Injections of fly nkd RNA result in very similar effects (FIG. 5a). Injection of 0.5 ng nkd RNA caused severe A-P truncations in approximately 52% (n=19) of the embryos, with milder effects in the rest, while 2.0 ng nkd RNA increased the penetrance to 97% (n=38), indicating a dose-response relationship.

Embryos with shortened A-P axes produced by injection of 2.0 ng Drosophila nkd RNA, FIG. 5(a) or the dominant inhibitory Xfz8 FIG. 5(b) into dorsal blastomere at 4 cell stage. Injection of water has no effect (FIG. 5c).

Antagonism of Wnt function apparently blocks cell movements that drive the elongation of the gastrula and neurula. These movements drive the elongation of ectodermal explants (animal caps) induced to form mesoderm by activin (FIG. 5d). Animal caps explanted from embryos injected with activin RNA (FIG. 5d) elongate (red arrow) when cultured. Wnt antagonists (such as NXfz8 or Xdd) block elongation of explants without inhibiting mesoderm induction. Injection of 2.0 ng nkd RNA into animal caps mimics this inhibitory effect, blocking elongation in response to activin (2.5 pg mRNA) in 90% of explants (n=47) (FIG. 5e) Simultaneous expression of activin and nkd RNA (FIG. 5e) blocks elongation. nkd RNA injected without activin has no effect on animal cap elongation.

Ventral expression of Wnts prior to the onset of zygotic transcription results in dorsal axis duplication that can be blocked by Wnt antagonists such as NXfz8, Xdd, or FrzB. nkd also blocks Wnt-mediated axis duplication. Ventral blastomere injection of 0.5 pg XWnt8 RNA resulted in ectopic dorsal axes in 56% of embryos (white arrow) (n=88) (FIG. 5f), approximately half of which formed complete anterior structures. Co-injection of 3.5 pg of nkd RNA reduced the frequency of ectopic axes to 42% (n=72), with only 10% of embryos forming complete anterior structures. Co-injection of 35 pg of nkd RNA gave only 19% (n=80) partial secondary axes, with no complete axes. At these doses, nkd RNA alone has no discernible effect on development when injected into either dorsal or ventral blastomeres. Higher doses (350 pg–2 ng) of nkd RNA injected alone into ventral blastomeres gives rise to ectopic heads (FIG. 5h), complete with eyes and cement gland. This striking phenotype has been attributed to antagonism of Wnt activity. Note the duplicated eye and cement gland (cg with arrow) and duplicated abdominal pigment (dashed line). The image in panel b has been previously published (Deardorff et al. (1998) *Development* 125:2687–2700). Scale bar=750 μm for FIGS. 5a–c, f–h; 375 μm for 5d, e.

These data show that nkd antagonizes Wg/Wnt signalling. Does nkd affect Wnt synthesis or transport, or determine how cells respond to Wnt? Because Wg and other Wnts are autoregulatory in many contexts, Nkd could affect the quantity or distribution of Wg either directly by controlling Wg synthesis or transport, or indirectly by reducing the positive feedback of Wg activity on its own synthesis. It can be noted that the first known gene expression defect in nkd mutants is in cells distant to Wg producers, suggesting nkd first acts in Wg-receiving cells. Additionally, nkd RNA injected into Xenpus embryos does not alter the accumulation of epitope-tagged XWnt8 protein, suggesting that nkd may block the response to XWnt8.

Inducible antagonists limit effective signal duration, range of action, or activity, and can act cell autonomously or non-autonomously. Near saturating genetic screens have revealed that nkd and patched (ptc; an inducible antagonist for Hh signalling) are the only Drosophila Wg or Hh pathway genes, other than Wg or Hh themselves, whose expression and genetic requirement are exclusively zygotic. All other known components for both signalling pathways are maternally provided. Evolutionary selective pressure apparently resists duplications of zygotically active inducible antagonist genes. Antagonist gene dosage must be carefully regulated in flies and vertebrates to balance the effects of the signals. In Drosophila, nkd and ptc mutations have haploinsufficient effects on cuticle pattern in combination with each other and with other segment polarity mutants. Altered regulation of both Wnt and Hh signalling in mice and humans is implicated in precancerous and cancerous cell growth. Just as vertebrate ptc1 regulates cell fates and is a key tumor suppressor gene, vertebrate Nkd-like proteins may be essential for restraining Wnt activity during development and possibly cancer progression.

Methods

Cloning of nkd $nkd^{7H16}$ and $nkd^{7E89}$ fail to complement the lethality of enhancer trap line I(3)4869. Homozygous I(3)4869 embryos have features of weak nkd alleles (see below). Precise excision of the I(3)4869 P element by transposase eliminated lethality and the weak nkd mutant phenotype. A 4 kb XbaI-XbaI genomic DNA fragment immediately 3' adjacent to the P-element insertion site in I(3)4869 was cloned by plasmid rescue and used to initiate the isolation of 80 kb of genomic DNA.

SSCP Analysis

SSCP analysis was performed using the MDE high-resolution gel from AT Biochem. 150 ng of genomic DNA was used as template. Primers 100–700 bp apart were used for SSCP-PCR. The sequences of the two primers which detect a nonsense mutation at codon 60 in $nkd^{7H16}$ are (SEQ ID NO:11) 5'-GCTGCTGGTCAGCGAACG-3' (CTP16) and (SEQ ID NO:12) 5'-TGATGAGACTGCTGCTTAC-3' (CBP17).

Fly stocks and P-element Mediated Transformation $wg^{IL114}$ was used at nonpermissive temperatures, mimicking a null wg allele, in FIGS. 3c and 4a,b. P element mediated transformation was performed on yw flies, using PπΔ2-3 as a source of transposase.

Heat-shock Mediated Nkd Overexpression and nkd Rescue

P[Hs-nkd] was made by cloning the Kpn-Kpn fragment from nkd cDNA clone C5 into Kpn-cut pABAL, which harbors the hsp70 promoter and 3' untranslated regions. The P[Hs-nkd] construct that was used for rescues lacks 5' and 3' untranslated regions and has a C terminal 9 amino acid human c-myc tag. Two independent transformant lines gave quantitatively similar results in Nkd overexpression experiments in both nkd mutant and wg/+ backgrounds. Most experiments used $nkd^{7H16}$; $nkd^{7E89}$ was rescued to a comparable degree by three independent insertions of P[Hs-nkd]. All known nkd alleles are embryonic lethals, and their cuticle phenotype severity can be scored as follows. "Strong" nkd mutants, (e.g. $nkd^{7H16}$ and $nkd^{7E89}$) secrete cuticles with a fully exteriorized head skeleton, widely split filzkorper (posterior spiracles), residual denticle belts only in A3 and/or A5 (or none at all), and are typically less than 75% of wild-type length. "Weak" nkd cuticles [e.g. I(3)4869 and $nkd^{42J1}$] have patchy cuticle loss, yet possess largely normal filzkorper and head skeleton, and are almost wild-type length. "Moderate" cuticles [e.g. $nkd^{9G33}$ and $nkd^{9H52}$] have a phenotype between weak and strong.

Nkd Antibody Production

Recombinant Nkd protein was made as a TrpE-Nkd fusion. The fusion protein was purified from BL21 pLysS *E. coli* lysates as inclusion bodies, cut from a SDS polyacrylamide gel, and injected with adjuvant into rabbits (Josman Labs). GST-Nkd fusion proteins to affinity purify anti-Nkd antisera were made by cloning similar fragments of the nkd cDNA into the vector pGEX-4T (Pharmacia). GST-Nkd fusion proteins were purified from BL21 pLysS *E. coli* using glutathione agarose beads coupled to an Aminolink Plus chromatography column (Pierce).

Immunocytochemistry

Embryos were washed and dechorionated in 50% bleach for 5 minutes, heat fixed for 10 seconds in a 90° C. solution of 100 mM NaCl and 0.05% Triton-X, and devitellinized in equal volumes of heptacne and methanol. Standard 4% formaldehyde fixation methods failed to reveal any specific staining pattern using both Nkd antisera. P[Hs-nkd] embryos were heat shocked at 37° C. for 30 minutes and allowed to recover for 30 minutes before fixation. Antibodies used: Nkd rabbit polyclonal antisera (1:100); biotinylated anti-rabbit secondary antibody (1:200). Staining was with biotinylated-Horseradish peroxidase (HRP)/avidin (Vectastain Elite ABC, Vector Laboratories) and 3,3'-diaminobenzidine as a substrate. For the Nkd stains in FIGS. 3a,b, 4 μl of a 6% solution of $NiCl_2$ was added to the staining reaction. Polyclonal antibodies made against two different parts of the Nkd protein (SmaI-SmaI fragment, amino acids 100–371; AseI-end, amino acids 679–928) give similar embryonic staining patterns. En monoclonal antibody supernatant was used at 1:1 and was performed on embryos fixed in 4% paraformaldehyde.

Immunoprecipitation

A 3–8 hr S-100 embryo extract was prepared in NP-40 buffer with proteinase inhibitor cocktail. 60 μl of extract was incubated with 1 μl of preimmune sera or 5 μl of Nkd rabbit polyclonal antisera. The antibodies were collected with protein A Sepharose beads, eluted, and separated on an 8% SDS-polyacrylamide gel. Antibodies used: Nkd rabbit polyclonal antisera (1:20); HRP-conjugated secondary antibody (1:20,000; Jackson Immunoresearch Labs). HRP activity was detected with Super Signal Chemiluminescent Substrate (Pierce).

In situ Hybridization

Whole mount in situ hybridization was performed with digoxigenin-labelled antisense RNA (Boehringer), using the 2.7 kb nkd coding region as a template. The probe was gently carbonated to produce fragments visualized on a gel in the 300 bp range.

UAS/Gal4-mediated nkd Overexpression

Native and myc-tagged versions of Nkd were cloned into pUAS-T (Brand et al. (1993) *Development* 118, 401–415) and transformed into flies. Constructs give similar phenotypes regardless of chromosome insertion site or Gal4 line. Dosage sensitivity of Wg pathway components to Nkd overexpression was tested using the alleles $porc^{I8}$, $Wg^{IL114}$, $wg^{CX4}$, $dsh^{477}$, $dsh^{V26}$, $zw3^{M11}$, $nkd^{7H16}$, $nkd^{7E89}$, and $arm^{YD35}$. B119-Gal4 and E132-Gal4 were used to drive UAS-nkd in these experiments, and three phenotypes were assayed for each Gal4 line in 50–1000 adults for each experiment.

Clonal Analysis

Balanced $nkd^{7H16}$ and $nkd^{9G33}$, originally generated on $h^1$, ru, cu,. ca chromosome, and st, $nkd^{7E89}$ which is $h^+$, were mated to w; FRT 80B, and nonbalancer progeny were mated to w; TM3/TM6 on food containing 50 μg/ml of Genticin (G418) at 26° C. Putative nkd, FRT80B/TM6 recombinants were mated with different nkd/TM3 alleles to test for complementation. Clones were induced between 3 and 48 hr AEL by mating w or +; nkd FRT 80B males with y, w, hs-FLP;;Z, FRT 80B females, where Z=P[y+,w+] for marking mutant bristles with yellow and mutant ommatidia with white, or Z=P[hs-πmyc] or P[Ubi-GFP] for marking mutant clones with anti-myc or GFP. Progeny were heat shocked at 37° for 30 min–2 hr. to induce expression of FLP recombinase, and males were examined for the presence of mutant yellow bristles. The leg study by Aloha-Avala (1958) was used to score bristle and quadrant identity of mutant and control clones. For imaginal tissues, rabbit anti-DII at 1:200; mouse anti-myc (9E10) at 1:1; mouse anti-Arm (N2-D71) at 1:5 were used. Clones were detected using either heat shock-mediated induction of πmyc or constitutive ubiquitous expression of GFP. For $h^1$, nkd clones, twin spots tended to be larger than clones, suggesting a cell autonomous lethal effect.

Xenopus Injections

The Nkd open reading frame with the C-terminal myc tag was subcloned into the expression vector pCS2 and mRNA was prepared by in vitro transcription. nkd mRNA +/−Xwnt8 mRNA was injected into the animal pole of one dorsal or ventral blastomere at the four-cell stage (10 nl/cell) and embryos were cultured until tadpole stage for scoring. For mesoderm induction assays, 10 nl nkd mRNA (0.2 ng/nl) and/or activin (0.25 pg/nl) mRNA was injected into the animal pole of fertilized eggs. At the blastula stage, animal caps were explanted, cultured until siblings reached the neurula stage, and then scored for elongation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule other than a naturally occurring chromosome comprising a sequence encoding a Nkd protein.

2. An isolated nucleic acid molecule according to claim 1, wherein said Nkd protein comprises the sequence set forth in SEQ ID NO:2.

3. An isolated nucleic acid molecule according to claim 2, wherein said nucleic acid comprises the nucleotide sequence set forth in SEQ ID NO:1.

4. An expression cassette comprising a transcriptional initiation region functional in an expression host, a nucleic acid having a sequence of the isolated nucleic acid according to claim 1 under the transcriptional regulation of said transcriptional initiation region, and a transcriptional termination region functional in said expression host.

5. A host cell comprising an expression cassette according to claim 4 as part of an extrachromosomal element or integrated into the genome of said host cell as a result of introduction of said expression cassette into said host cell, and the cellular progeny of said host cell.

6. A host cell comprising a nucleic acid according to claim 1 as part of an extrachromosomal element or integrated into the genome of said host cell as a result of introduction of an expression cassette into said host cell, and the cellular progeny of said host cell.

7. An isolated nucleic acid molecule according to claim 1, wherein said Nkd protein is a drosophila, human, or mouse Nkd protein, and further wherein said Nkd protein is an antagonist for Wnt signaling and comprises a single EF-hand domain.

8. An isolated nucleic acid molecule that hybridizes under stringent conditions of 50° C. or higher in the presence of 0.1×SSC to the nucleic acid sequence of SEQ ID NO:1.

* * * * *